(12) United States Patent
Suehle et al.

(10) Patent No.: US 10,067,118 B2
(45) Date of Patent: Sep. 4, 2018

(54) SINGLE MOLECULE FILTER AND SINGLE MOLECULE ELECTROGRAPH, AND PROCESS FOR MAKING AND USING SAME

(71) Applicant: NATIONAL INSTITUTE OF STANDARDS AND TECHNOLOGY, Gaithersburg, MD (US)

(72) Inventors: John S. Suehle, Westminster, MD (US); John J. Kasianowicz, Darnestown, MD (US); Arvind Balijepalli, Washington, DC (US); Joseph W. Robertson, Washington, DC (US); Jessica Benjamini, Rockville, MD (US)

(73) Assignee: NATIONAL INSTITUTE OF STANDARDS AND TECHNOLOGY, Gaithersburg, MD (US)

( * ) Notice: Subject to any disclaimer, the term of this patent is extended or adjusted under 35 U.S.C. 154(b) by 471 days.

(21) Appl. No.: 14/872,128

(22) Filed: Sep. 30, 2015

(65) Prior Publication Data
US 2016/0033451 A1 Feb. 4, 2016

Related U.S. Application Data

(60) Provisional application No. 62/060,708, filed on Oct. 7, 2014.

(51) Int. Cl.
*G01N 27/48* (2006.01)
*G01N 33/487* (2006.01)

(52) U.S. Cl.
CPC .............. *G01N 33/48721* (2013.01)

(58) Field of Classification Search
CPC .................................. G01N 33/48721
See application file for complete search history.

(56) References Cited

U.S. PATENT DOCUMENTS

| 5,466,351 A | 11/1995 | Rampal et al. |
| 2011/0120868 A1* | 5/2011 | Lindsay ............. B82Y 15/00 204/452 |

* cited by examiner

*Primary Examiner* — J. Christopher Ball
(74) *Attorney, Agent, or Firm* — Office of Chief Counsel for National Institute of Standards and Technology

(57) ABSTRACT

A single molecule filter includes: a membrane including: a first surface; a second surface; and a membrane aperture disposed in the membrane and traversing the membrane from the first surface to the second surface, the membrane aperture provided to communicate a single molecule across the membrane; and a nanotube disposed on the membrane and including: a first end disposed on the first surface of the membrane; a second end disposed distal to the first surface; and a tubular aperture extending along the nanotube from the first end to the second end, the tubular aperture provided to communicate the single molecule from the second end of the nanotube to the membrane aperture.

28 Claims, 25 Drawing Sheets

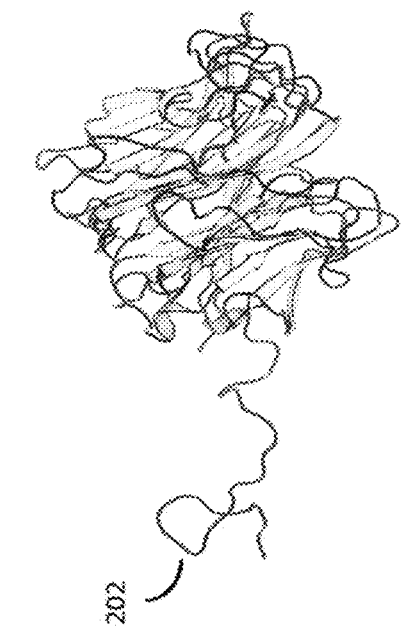
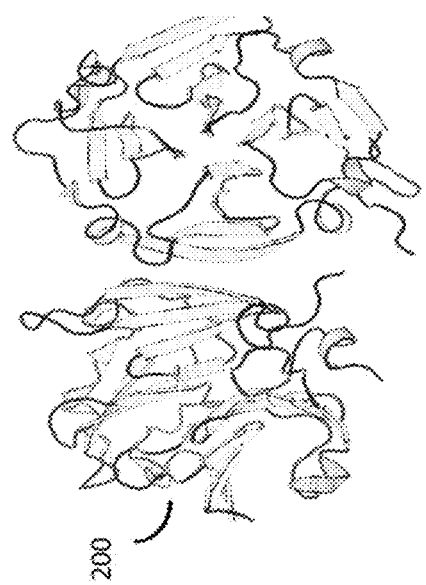
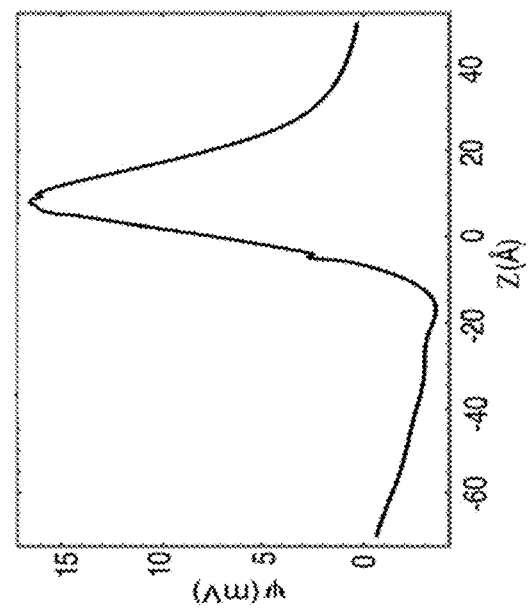
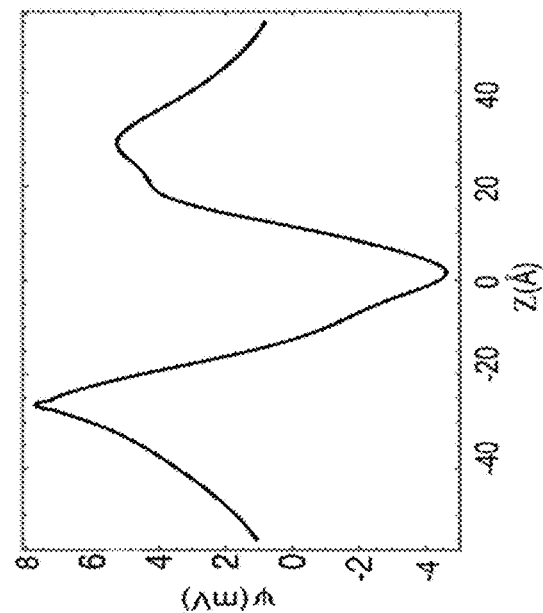
FIG. 35

SINGLE MOLECULE FILTER AND SINGLE MOLECULE ELECTROGRAPH, AND PROCESS FOR MAKING AND USING SAME

CROSS REFERENCE TO RELATED APPLICATIONS

This application claims the benefit of U.S. Provisional Patent Application Ser. No. 62/060,708 filed Oct. 7, 2014, the disclosure of which is incorporated herein by reference in its entirety.

STATEMENT REGARDING FEDERALLY SPONSORED RESEARCH

This invention was made with United States government support from the National Institute of Standards and Technology. The government has certain rights in the invention.

BRIEF DESCRIPTION

Disclosed is a single molecule filter comprising: a membrane comprising: a first surface; a second surface; and a membrane aperture disposed in the membrane and traversing the membrane from the first surface to the second surface, the membrane aperture provided to communicate a single molecule across the membrane; and a nanotube disposed on the membrane and comprising: a first end disposed on the first surface of the membrane; a second end disposed distal to the first surface; and a tubular aperture extending along the nanotube from the first end to the second end, the tubular aperture provided to communicate the single molecule from the second end of the nanotube to the membrane aperture.

Further disclosed is a single molecule detector comprising: a single molecule filter comprising: a membrane comprising: a first surface; a second surface; and a membrane aperture disposed in the membrane and traversing the membrane from the first surface to the second surface, the membrane aperture provided to communicate a single molecule across the membrane; a nanotube disposed on the membrane and comprising: a first end disposed on the first surface of the membrane; a second end disposed distal to the first surface; and a tubular aperture extending along the nanotube from the first end to the second end, the tubular aperture provided to communicate the single molecule from the second end of the nanotube to the membrane aperture; a primary electrode disposed: proximate to and opposing the second end of the nanotube, and distal to the second surface; and a secondary electrode disposed: proximate to and opposing the second surface, distal to the nanotube, and opposing the primary electrode.

Additionally disclosed is a process for detecting a single molecule, the process comprising: providing a single molecule detector that comprises: a single molecule filter comprising: a membrane comprising: a first surface; a second surface; and a membrane aperture disposed in the membrane and traversing the membrane from the first surface to the second surface, the membrane aperture provided to communicate a single molecule across the membrane; a nanotube disposed on the membrane and comprising: a first end disposed on the first surface of the membrane; a second end disposed distal to the first surface; and a tubular aperture extending along the nanotube from the first end to the second end, the tubular aperture provided to communicate the single molecule from the second end of the nanotube to the membrane aperture; a primary electrode disposed: proximate to and opposing the second end of the nanotube, and distal to the second surface; a secondary electrode disposed: proximate to and opposing the second surface, distal to the nanotube, and opposing the primary electrode; and a container in which the single molecule filter, the primary electrode, and the secondary electrode are disposed, the single molecule filter partitioning the container into a first compartment and a second compartment with the single molecule filter separating the first compartment from the second compartment such that the tubular aperture and the membrane aperture solely communicate the single molecule between the first compartment and the second compartment; disposing a composition comprising the single molecule in the first compartment; and communicating the single molecule from the first compartment to the second compartment through the tubular aperture and the membrane aperture to detect the single molecule.

Also disclosed is a process for making a single molecule filter, the process comprising: providing a substrate comprising: a first layer comprising a first surface; and a second layer disposed on the first layer and comprising a second surface; removing a portion of the second layer to form a membrane aperture bounded by a membrane wall; disposing a catalyst on the first surface of the first layer; contacting the catalyst with a precursor; forming a nanocolumn interposed between the catalyst and the first layer, the nanocolumn comprising a reaction product of the precursor; oxidizing a portion of the first layer at the first surface to form an interfacial layer, the interfacial layer comprising a semiconductor oxide; oxidizing a portion of the nanocolumn to form a nanotube disposed on the interfacial layer, the nanotube comprising: the semiconductor oxide; a first end disposed on the first surface of the membrane; and a second end disposed distal to the first surface; removing the nanocolumn to form a tubular aperture extending along the nanotube from the first end to the second end, the tubular aperture provided to communicate a single molecule from the second end of the nanotube to the membrane aperture; extending the membrane wall through the first layer by removing a portion of the first layer so that the membrane aperture and the tubular aperture provide communication of the single molecule from the second end of the nanotube to the second surface of the across the membrane through the tubular aperture and the membrane aperture to make the single molecule filter.

BRIEF DESCRIPTION OF THE DRAWINGS

The following descriptions should not be considered limiting in any way. With reference to the accompanying drawings, like elements are numbered alike.

FIG. 35 shows a protein biomarker and graph of electrostatic potential versus position along a long axis of the protein biomarker according to Example 2.

DETAILED DESCRIPTION

A detailed description of one or more embodiments is presented herein by way of exemplification and not limitation.

It has been discovered that articles and processes herein provide unique identification of a single molecule disposed in a composition. A single molecule filter that includes a nanotube can be produced from a nanocolumn disposed on a membrane, which can be electrically insulating. The nanotube communicates the single molecule through a tubular aperture disposed in the nanotube to an opposite side of the membrane. Such communication of the single molecule can occur by subjecting the single molecule filter to an electric field. Moreover, a single molecule electrograph can monolithically include the single molecule filter to detect communication of the single molecule through the single molecule filter. The single molecule electrograph advantageously is configured to produce a change in drain current in response to presence of the single molecule in the tubular aperture.

Figure 1:
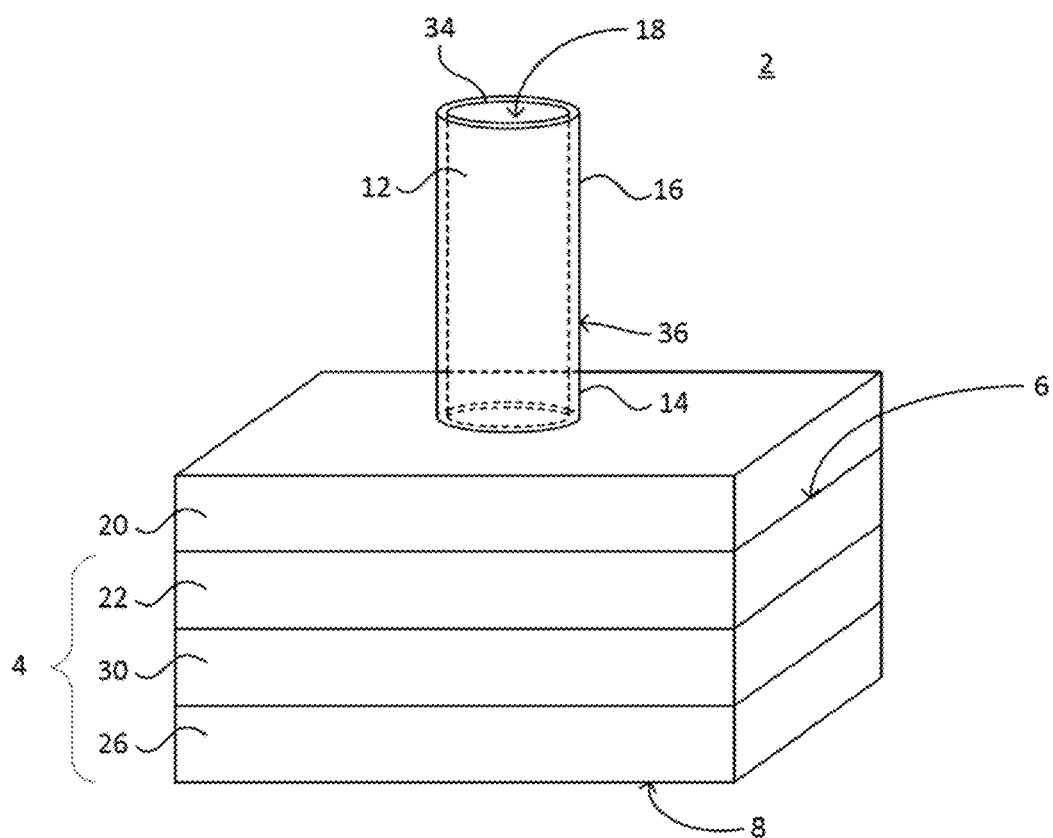
FIG. 1 shows a perspective view of a single molecule filter.
Figure 2:
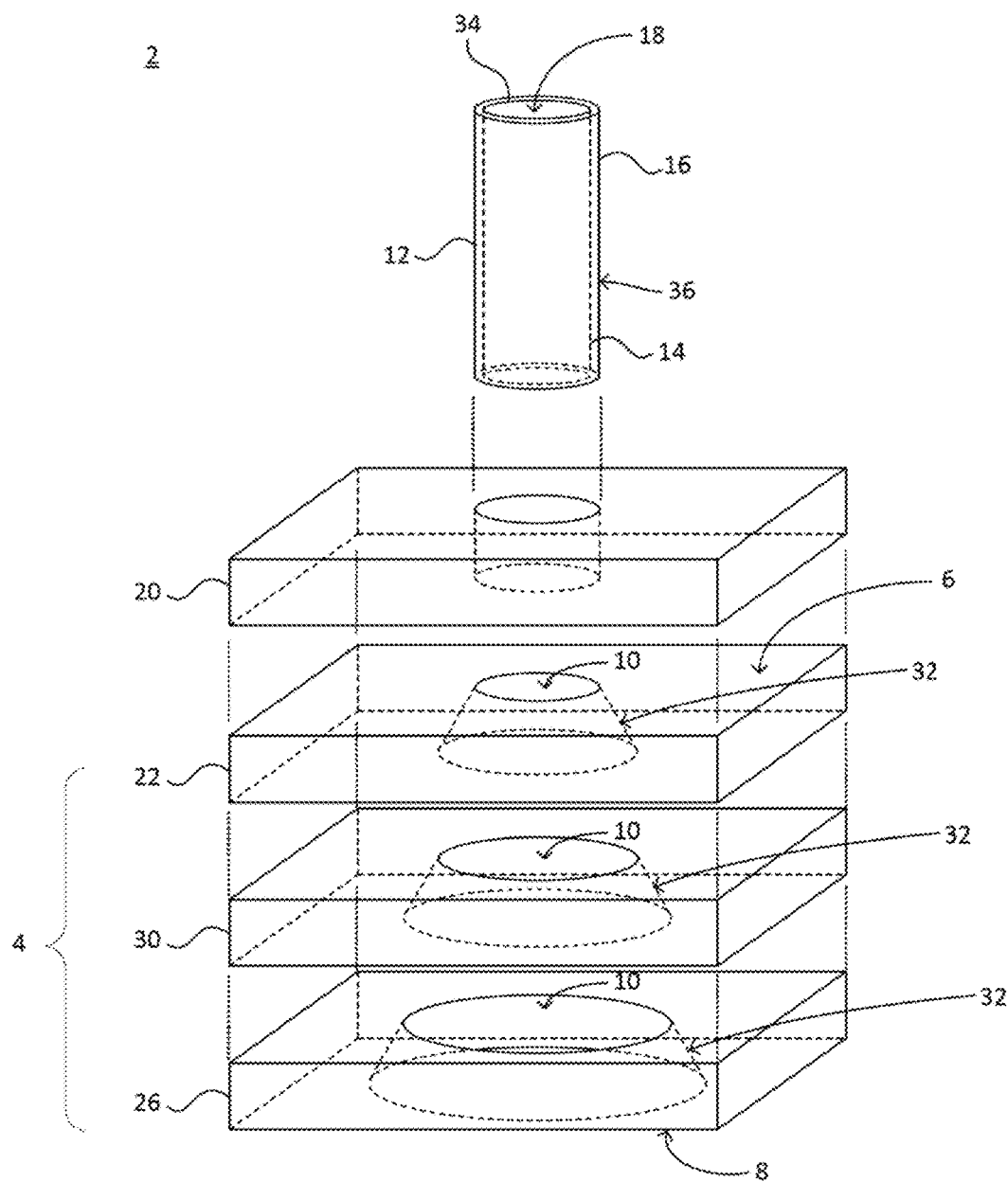
FIG. 2 shows an exploded view of the single molecule filter shown in FIG. 1.
Figure 3:
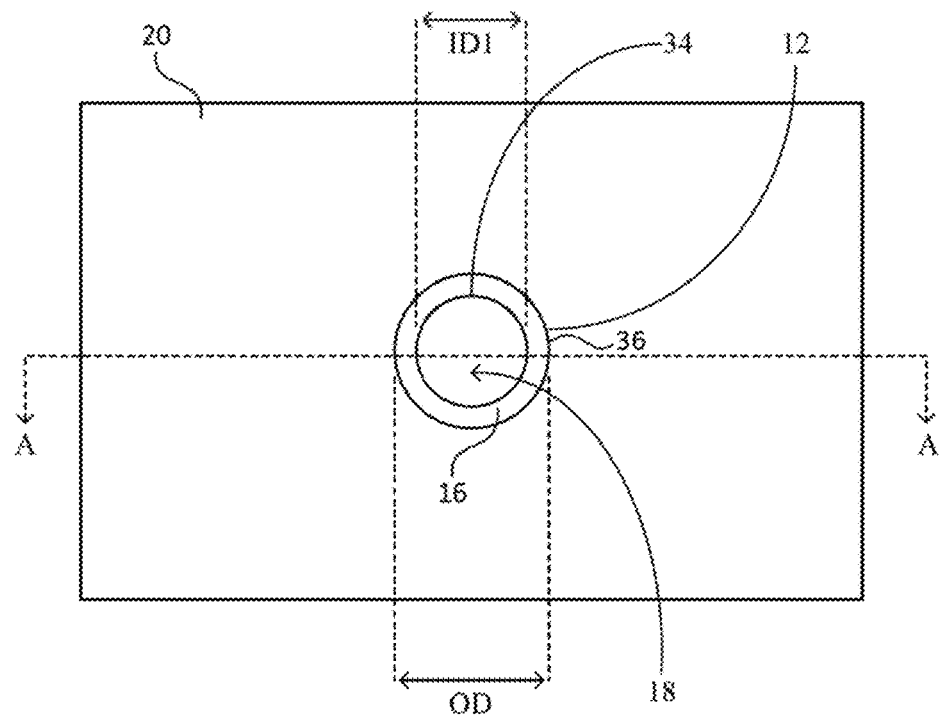
FIG. 3 shows a top view of the single molecule filter shown in FIG. 1.
Figure 4:
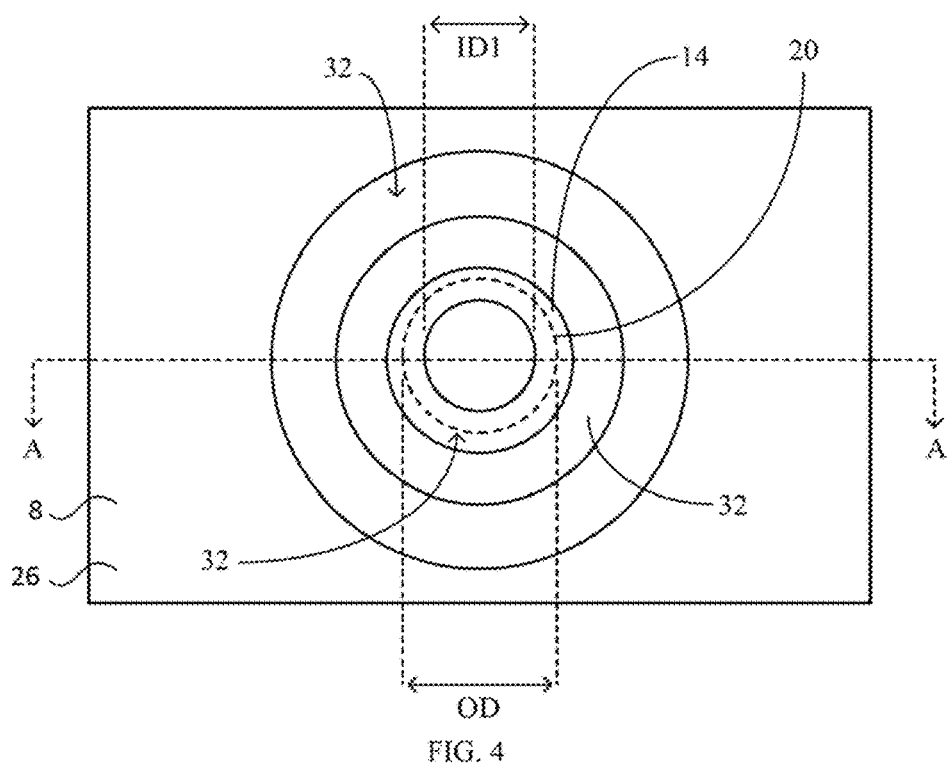
FIG. 4 shows a bottom view of the single molecule filter shown in FIG. 1.
Figure 5:
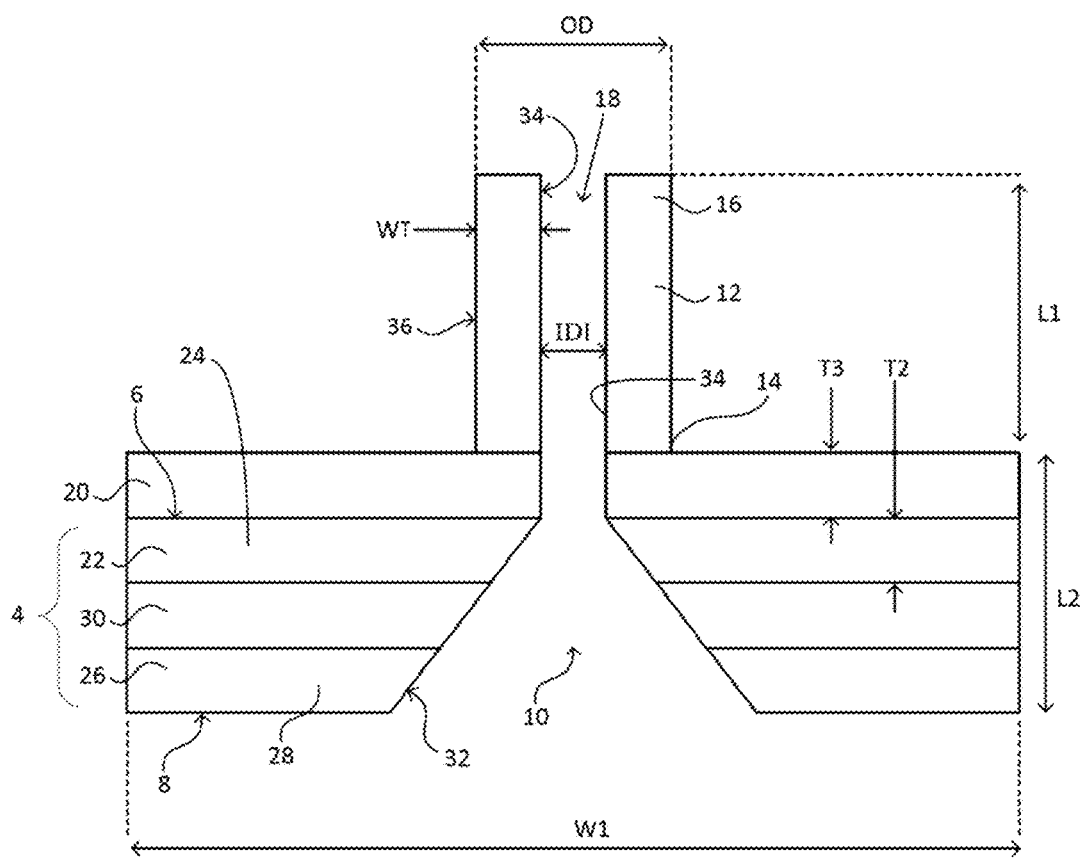
FIG. 5 shows a cross section along line A-A of the single molecule filter shown in FIG. 3.

In an embodiment, as shown in FIG. 1 (a perspective view of single molecule filter 2), FIG. 2 (exploded view of single molecule filter 2), FIG. 3 (top view of single molecule filter 2), FIG. 4 (bottom view of single molecule filter 2), and FIG. 5 (cross-section of single molecule filter 2 along line A-A shown in FIG. 3), single molecule filter 2 includes membrane 4 that includes first surface 6, second surface 8, and membrane aperture 10 disposed in membrane 4 and traversing membrane 4 from first surface 6 to second surface 8. Membrane aperture 10 is provided to communicate the single molecule across membrane 4. single molecule filter 2 also includes nanotube 12 disposed on membrane 4 and includes first end 14 disposed on first surface 6 of membrane 4, second end 16 disposed distal to first surface 6, and tubular aperture 18 extending along nanotube 12 from first end 14 to second end 16. Tubular aperture 18 is provided to communicate the single molecule from second end 16 of nanotube 12 to membrane aperture 10.

Single molecule filter 2 further includes interfacial layer 20 disposed on first surface 6 and interposed between first end 14 of nanotube 12 and first surface 6 of membrane 4. In some embodiments, membrane 4 can include a plurality of layers such as first layer 22 disposed on second layer 26. First layer 22 includes first semiconductor 24 and first surface 6. Second layer 26 opposes first layer 22 and includes second semiconductor 28 and second surface 8.

The plurality of layers of membrane 4 also can include intermediate layer 30 interposed between first layer 22 and second layer 26. Membrane wall 32 bounds membrane aperture 10, extends in an interior space of membrane 4 from second surface 8 to first surface 6, and is in fluid communication with tubular aperture 18.

In single molecule filter 2, nanotube 12 includes inner wall 34 that bounds tubular aperture 18 and outer wall 36 that circumscribes nanotube 12. Nanotube further includes length L1, outer diameter OD, inner diameter ID1, wall thickness WT, and an aspect ratio that is a ratio of length L1 to inner diameter ID1. Further, first layer 22 of membrane 4 has thickness T2, and interfacial layer 20 has thickness T3. Membrane 4 and interfacial layer 20 have a total thickness L2. single molecule filter 2 has width W1.

Figure 6:
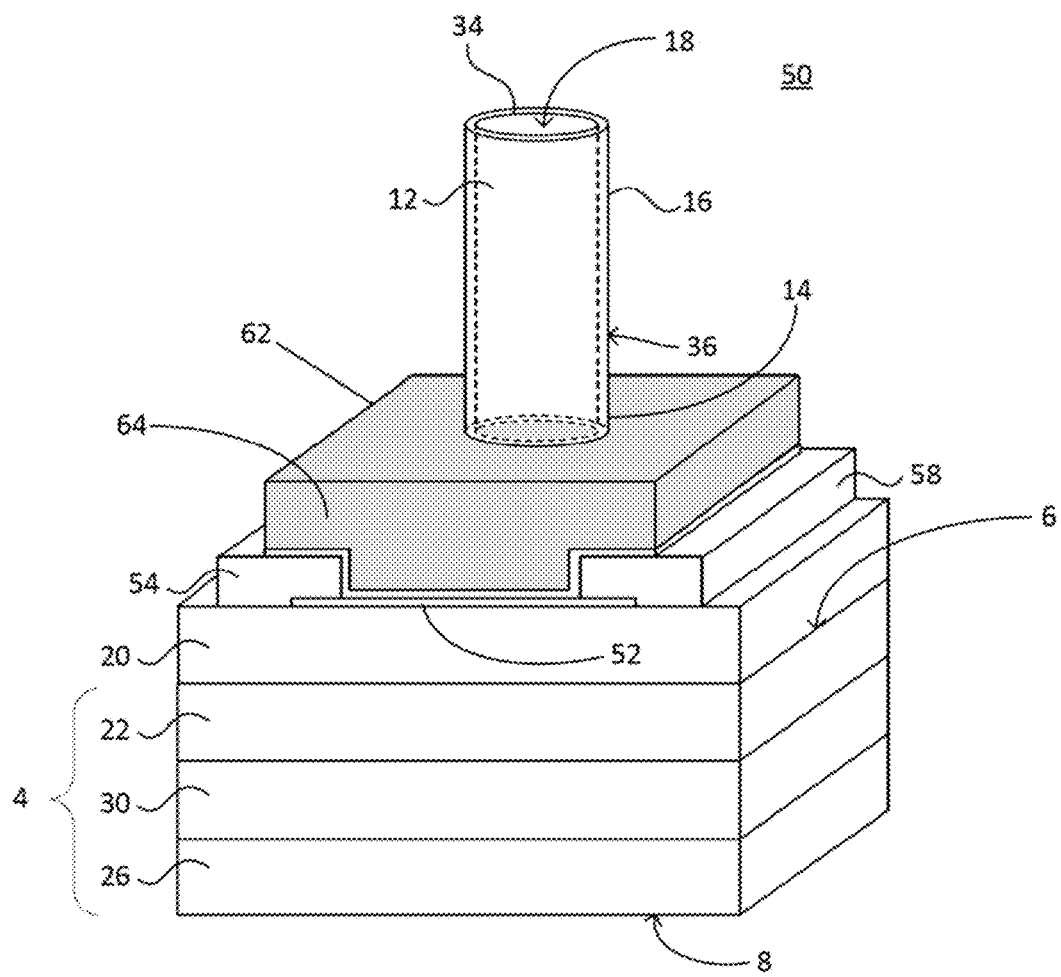
FIG. 6 shows a perspective view of a single molecule electrograph.
Figure 7:
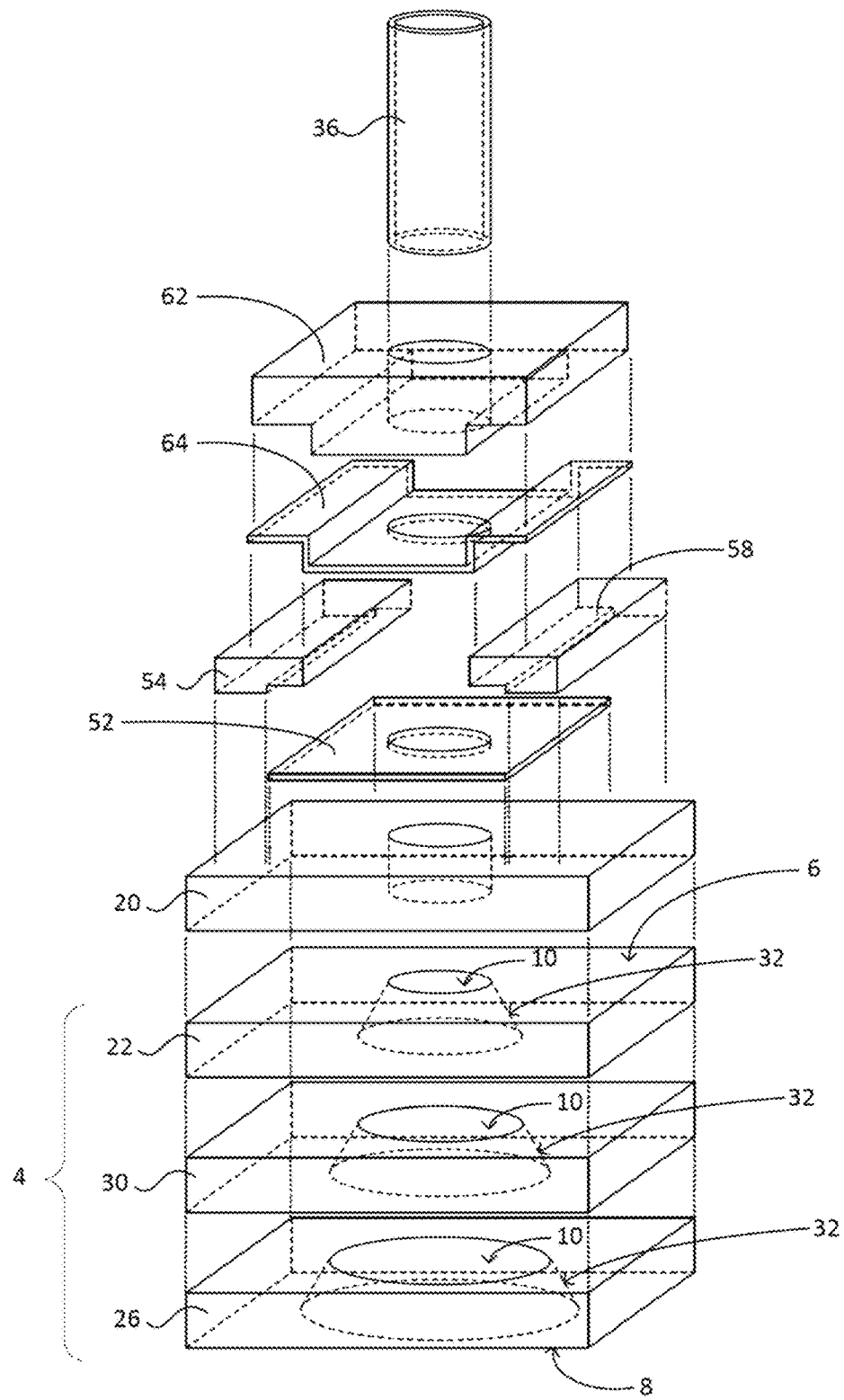
FIG. 7 shows an exploded view of the single molecule electrograph shown in FIG. 6.
Figure 8:
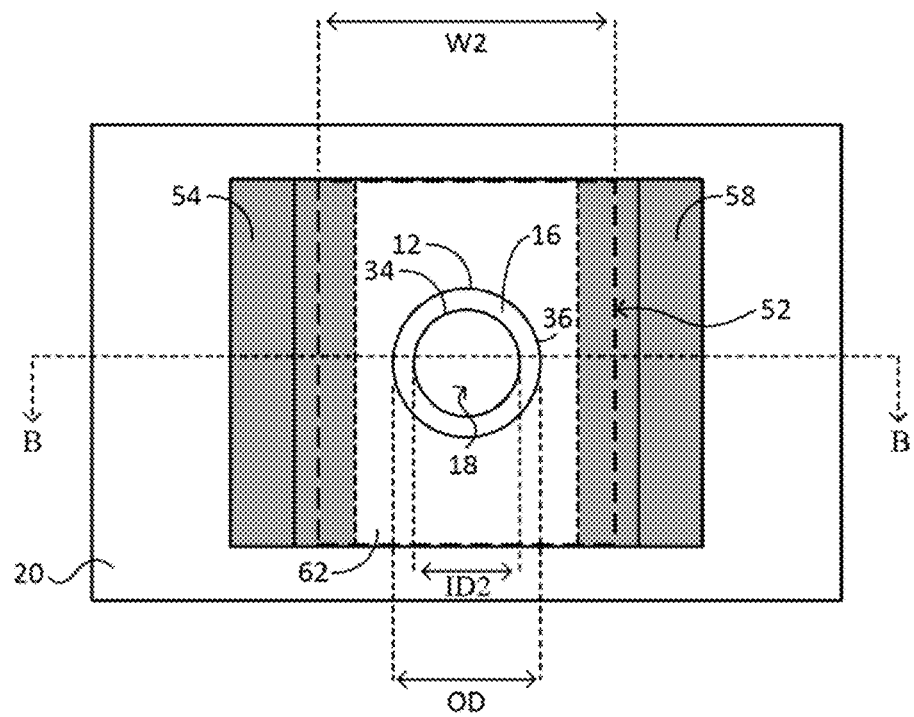
FIG. 8 shows a top view of the single molecule electrograph shown in FIG. 6.
Figure 9:
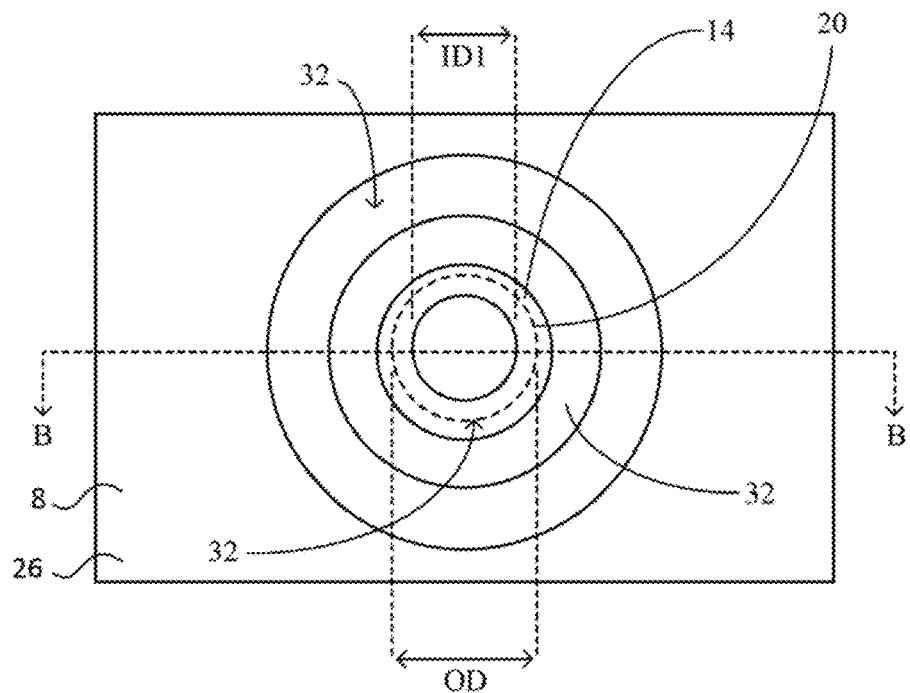
FIG. 9 shows a bottom view of the single molecule electrograph shown in FIG. 6.
Figure 10:
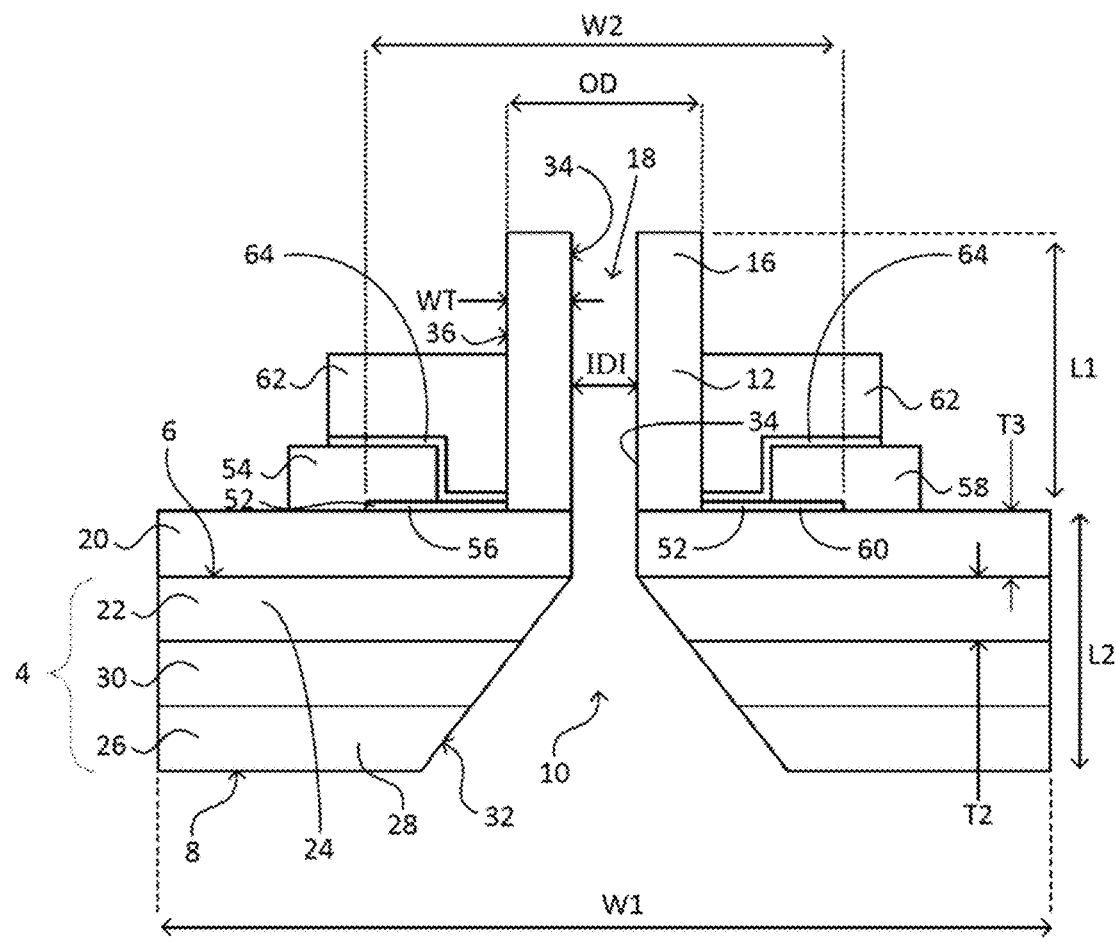
FIG. 10 shows a cross section along line B-B of single molecule electrograph shown in FIG. 8.

In an embodiment, with reference to FIG. 6 (a perspective view of single molecule electrograph 50), FIG. 7 (exploded view of single molecule electrograph 50), FIG. 8 (top view of single molecule electrograph 50), FIG. 9 (bottom view of single molecule electrograph 50), and FIG. 10 (cross-section of single molecule electrograph 50 along line A-A shown in FIG. 8), single molecule electrograph 50 includes membrane 4 that includes first surface 6, second surface 8, and membrane aperture 10 disposed in membrane 4 and traversing membrane 4 from first surface 6 to second surface 8. Membrane aperture 10 is provided to communicate the single molecule across membrane 4. single molecule electrograph 50 also includes nanotube 12 disposed on membrane 4 and includes first end 14 disposed on first surface 6 of membrane 4, second end 16 disposed distal to first surface 6, and tubular aperture 18 extending along nanotube 12 from first end 14 to second end 16. Tubular aperture 18 is provided to communicate the single molecule from second end 16 of nanotube 12 to membrane aperture 10.

Further, single molecule electrograph 50 further includes interfacial layer 20 disposed on first surface 6 and interposed between first end 14 of nanotube 12 and first surface 6 of membrane 4. In some embodiments, membrane 4 can include a plurality of layers such as first layer 22 disposed on second layer 26. First layer 22 includes first semiconductor 24 and first surface 6. Second layer 26 opposes first layer 22 and includes second semiconductor 28 and second surface 8.

The plurality of layers of membrane 4 also can include intermediate layer 30 interposed between first layer 22 and second layer 26. Membrane wall 32 bounds membrane aperture 10, extends in an interior space of membrane 4 from second surface 8 to first surface 6, and is in fluid communication with tubular aperture 18.

In single molecule electrograph 50, nanotube 12 includes inner wall 34 that bounds tubular aperture 18 and outer wall 36 that circumscribes nanotube 12. Nanotube further includes length L1, outer diameter OD, inner diameter ID1, wall thickness WT, and an aspect ratio that is a ratio of length L1 to inner diameter ID1. Further, first layer 22 of membrane 4 has thickness T2, and interfacial layer 20 has thickness T3. Membrane 4 and interfacial layer 20 have a total thickness L2. single molecule electrograph 50 has width W1.

In this configuration, single molecule electrograph 50 includes transistor 66 disposed on interfacial layer 20 and surroundingly disposed around nanotube 12. Transistor 66 includes active element 52, source electrode 54, drain electrode 58, gate electrode 62, and gate dielectric 64. Active element 52 is surroundingly disposed around first end 14 of nanotube 12 and disposed on interfacial layer 20. Source electrode 54 is disposed on interfacial layer 20 and first portion 56 of active element 52. Drain electrode 58 this disposed on interfacial layer 20 and second portion 60 of active element 52. Gate electrode 62 is disposed on source electrode 54, drain electrode 58, and active element 52. Gate dielectric 64 is interposed between gate electrode 62 and source electrode 54 and also between gate electrode 62 and training electrode 58.

Active element 52 is provided to communicate a drain current between source electrode 54 and drain electrode 58 in a presence of a gate voltage, source voltage, and drain voltage respectively subjected to gate electrode 62, source electrode 54, and drain electrode 58 when a gate voltage exceeds a threshold value determined by the properties of active element 52. Here, active element 52 has width W2. Accordingly, a ratio of width W2 to outer diameter OD of nanotube 12 is selected to provide capacitive coupling between transistor 66 and a single molecule when the single molecule is present in tubular aperture 18. The capacitive coupling provides for an electrical signal to be produced from single molecule electrograph 50 in response to presence of the single molecule in tubular aperture 18 of nanotube 12 such that a change in drain current occurs when the single molecule is present in tubular aperture 18 relative to the drain current with the single molecule is absent from tubular aperture 18.

Figure 11:
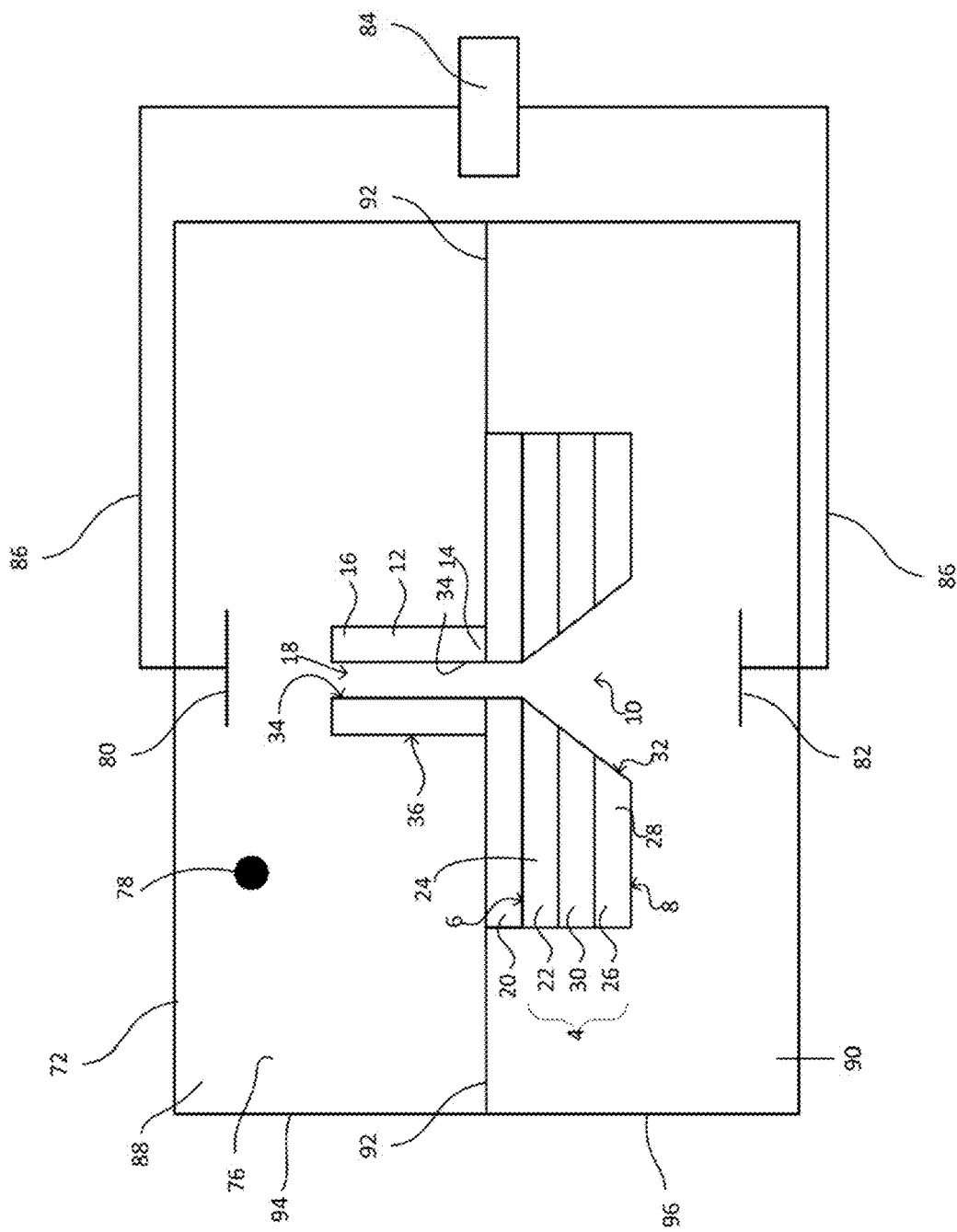
FIG. 11 shows a single molecule detector.

According to an embodiment, as shown in FIG. 11, single molecule detector 70 includes single molecule filter 2 disposed in container 72. Container 72 includes wall 74 to contain single molecule filter 2 and in which composition 76 that includes single molecule 78 can be disposed. Primary electrode 80 or secondary electrode 82 optionally can be disposed in container 78. Power supply 84 can be provided to be in electrical communication with primary electrode 80 or secondary electrode 82 via electrical line 86. In some embodiments, primary electrode 80 is disposed proximate to and opposing second end 16 of nanotube 12 and distal to second surface 8. Secondary electrode 82 can be disposed proximate to and opposing second surface 8 distal to nanotube 12 and opposing primary electrode 80.

Here, single molecule filter 2 partitions container 72 and separates container 72 into first compartment 88 and second compartment 90 such that tubular aperture 18 and membrane aperture 10 solely communicate single molecule 78 between first compartment 88 and second compartment 90. In some embodiments, single molecule filter 2 can be disposed on support 92 such that support 92 forms a leak-tight interface with single molecule filter 2. Support 92 can be attached to container 72 so that first compartment 88 and second compartment 90 are not in fluid communication except through tubular aperture 18. In some embodiments, support 92 or single molecule filter 2 can include a flow hole (not shown) to provide fluid communication between first compartment 88 and second compartment 90. In a certain embodiment, the flow hole and which can be sealed (e.g., with a valve or the like) to eliminate fluid communication between first compartment 88 and second compartment 90.

In an embodiment, container 72 can include can include an electrically insulating member (not shown) that in combination with single molecule filter 2 or support 92 partitions and separates first compartment 88 and second compartment 90. Here, the electrically insulating member can be an elastomeric (or rigid) material (e.g., polymer, glass, ceramic, or the like) that is disposed in wall 74 such that first wall 94 of first compartment 88 is electrically insulated from second wall 96 of second compartment 90. In this embodiment, primary electrode 80 could be part of first wall 94, or secondary electrode 82 could be part of second wall 96.

Figure 12:
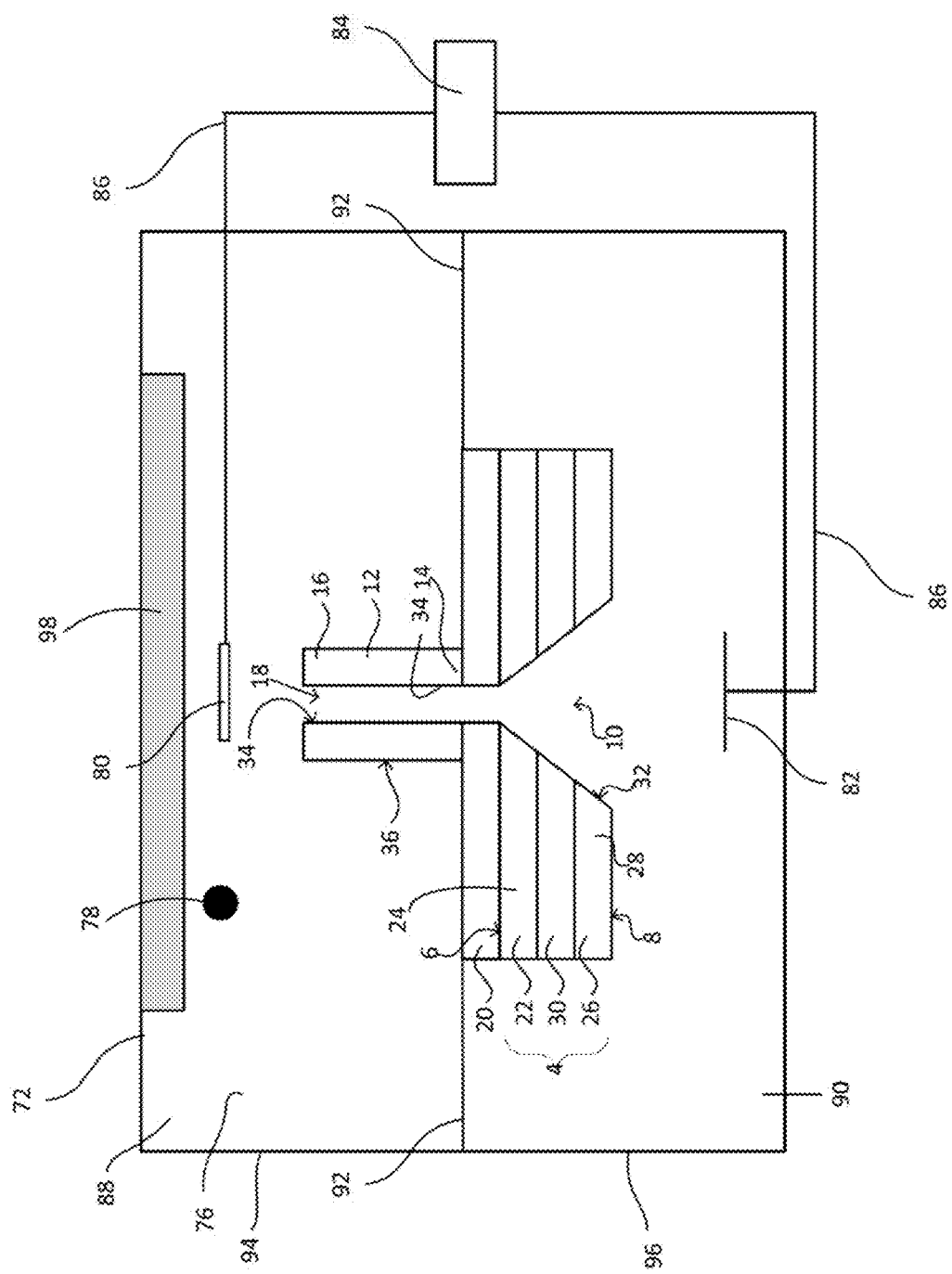
FIG. 12 shows a container that includes a pressure member.

In an embodiment, as shown in FIG. 12, container 74 includes a pressure member 98 to subject composition 76 to a hydrostatic pressure. Here, composition 76 can be subjected to a first hydrostatic pressure in first compartment 88 that is greater than a second hydrostatic pressure in second compartment 90 such that composition 76 is stimulated to be communicated through tubular aperture 18 of single molecule filter 2. Exemplary types of pressure member 98 include a piston to decrease a volume of first compartment 88, a valve in communication with a fluid source having a selected pressure of a fluid (e.g., composition 76), and the like.

Figure 13:
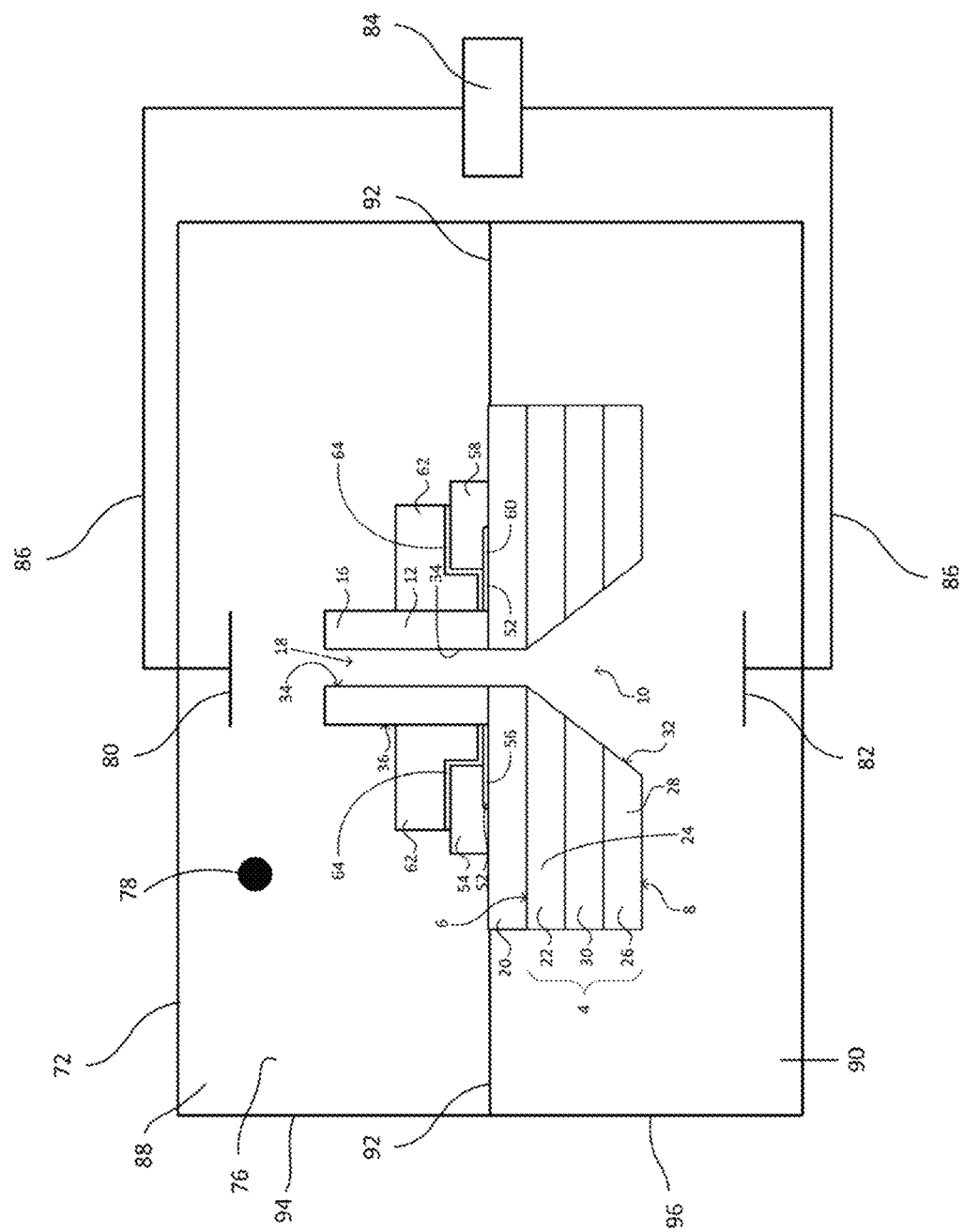
FIG. 13 shows a single molecule detector that includes a single molecule electrograph disposed in a container.

According to an embodiment, as shown in FIG. 13, single molecule detector 70 includes single molecule electrograph 50 disposed in container 72. Container 72 includes wall 74 to contain single molecule filter 2 and in which composition 76 that includes single molecule 78 can be disposed. Primary electrode 80 or secondary electrode 82 optionally can be disposed in container 78. Power supply 84 can be provided to be in electrical communication with primary electrode 80 or secondary electrode 82 via electrical line 86. In some embodiments, primary electrode 80 is disposed proximate to and opposing second end 16 of nanotube 12 and distal to second surface 8. Secondary electrode 82 can be disposed proximate to and opposing second surface 8 distal to nanotube 12 and opposing primary electrode 80.

Here, single molecule electrograph 50 partitions container 72 and separates container 72 into first compartment 88 and second compartment 90 such that tubular aperture 18 and membrane aperture 10 solely communicate single molecule 78 between first compartment 88 and second compartment 90. In some embodiments, single molecule electrograph 50 can be disposed on support 92 such that support 92 forms a leak-tight interface with single molecule electrograph 50. Support 92 can be attached to container 72 so that first compartment 88 and second compartment 90 are not in fluid communication except through tubular aperture 18. In some embodiments, support 92 or single molecule electrograph 50 can include a flow hole (not shown) to provide fluid communication between first compartment 88 and second compartment 90. In a certain embodiment, the flow hole and which can be sealed (e.g., with a valve or the like) to eliminate fluid communication between first compartment 88 and second compartment 90.

In an embodiment, container 72 can include can include an electrically insulating member (not shown) that in combination with single molecule electrograph 50 or support 92 partitions and separates first compartment 88 and second compartment 90. Here, the electrically insulating member can be an elastomeric (or rigid) material (e.g., polymer, glass, ceramic, or the like) that is disposed in wall 74 such that first wall 94 of first compartment 88 is electrically insulated from second wall 96 of second compartment 90. In this embodiment, primary electrode 80 could be part of first wall 94, or secondary electrode 82 could be part of second wall 96.

In an embodiment, container 74 includes a pressure member 98 to subject composition 76 to a hydrostatic pressure. Here, composition 76 can be subjected to a first hydrostatic pressure in first compartment 88 that is greater than a second hydrostatic pressure in second compartment 90 such that composition 76 is stimulated to be communicated through tubular aperture 18 of single molecule electrograph 50.

Various materials can be used to make or use single molecule filter 2, single molecule electrograph 50, or single molecule detector 70. In an embodiment, membrane 4 includes first layer 22, second layer 26, intermediate layer 30, or a combination thereof on which is disposed nanotube 12 and interfacial layer 22.

First layer 22, second layer 26, and intermediate layer 30 independently can be a material selected on which nanotube 12 can be disposed and through which single molecule 78 can be communicated across membrane 4 through tubular aperture 18 and membrane aperture 10. According to an embodiment, first layer 22, second layer 26, and intermediate layer 30 independently include a semiconductor. An exemplary semiconductor is an element from group 11, 12, 13, 14, 15, or 16 (IUPAC nomenclature, which respectively is identical to group I, II, III, IV, V, or VI) of the periodic table such as a Si, Ga, Ge, As, In, Sn, Sb, Te, At, Hf, Zn, and the like, or a combination thereof. According to an embodiment, the semiconductor is a compound semiconductor such as SiC, SiGe, GaN; a group 13-15 (also referred to as a group III-V) semiconductor such as AlSb, AlAs, Aln, AlP, BN, GaSb, GaAs, GaN, GaP, InSb, InAs, InN, InP, and the like; a group 12-16 (group II-VI) semiconductor such as CdSe, CdS, CdTe, ZnO, ZnSe, ZnS, ZnTe, and the like; a group 11-17 (group I-VII) semiconductor such as CuCl and the like; a group 14-16 (group IV-VI) semiconductor such as PbS, PbTe SnS, and the like; a layer semiconductor such as $PbI_2$, $MoS_2$, GaSe, and the like; an oxide semiconductor such as CuO, $Cu_2O$, and the like; (Al,Ga)N, (Al,Ga)As, (In,Ga)As, (Al,Ga)Sb, (In,Ga)Sb, as well as nitride, arsenide, antimonide quaternary III-V alloys, or a combination thereof. Examples of II-VI alloys include, but are not limited to CdSe, CdTe, CdS, ZnSe, and combinations thereof. Examples of Group III-V ternary alloys include, but are not limited to, (Ga,Al)As, (In,Ga)As, and combinations thereof. Exemplary Group III-V quaternary alloys include (Ga,In)(As,P), (In,Al,Ga)Sb, and the like. Exemplary Group III-nitride alloys include (Ga,Al)N, (Ga,In)N, (Al,In)N, (Ga,Al,In)N, and combinations thereof. Quaternary alloys of the above may also be employed.

The semiconductor also can include a supplemental element such as C, H, N, Li, Na, K, Mg, Ca, Sr, Ba, Bi, B, Al, P, S, O, and the like in an amount typically less than an amount of the semiconductor. In an embodiment, the semiconductor includes silicon, and the silicon is optionally doped. According to an embodiment, the semiconductor is an intrinsic semiconductor or an extrinsic semiconductor doped with a selected dopant, e.g., a p-dopant or an n-dopant. In one embodiment, the semiconductor includes a p-dopant. In another embodiment, the semiconductor includes an n-dopant. In a particular embodiment, the semiconductor is p-doped Si. In one embodiment, the semiconductor is n-doped Si. The semiconductor can be produced from, e.g., commercially available semiconductor grade p-doped Si having a particular crystalline orientation, e.g., having Miller indices <111>, <100>, and the like. The semiconductor can be amorphous, polycrystalline, or a single crystal. In an embodiment, the semiconductor has a stacked structure that includes a plurality of semiconductor layers such as by forming films as SiGe/Si/SiGe/Si on the Si semiconductor. In some embodiments, the semiconductor includes crystalline domains among amorphous material.

In a particular embodiment, first layer 22, second layer 26, intermediate and layer 30 respectively are Si <111>, silicon dioxide, and Si <100>. Without wishing to be bound by theory, nanotube 12 can be grown on interfacial layer 20 such that a spatial orientation of nanotube 12 and crystallinity and morphology of interfacial layer 20 depend on a composition and atomic ordering of first layer 22. In an embodiment, nanotube 12 is vertically aligned to first surface 22 of membrane 4 such that tubular aperture 18 extends substantially orthogonal to first surface 22. In some embodiments, nanotube 12 is disposed on interfacial layer 20 such that tubular aperture 18 extends an acute angle (e.g., from 0° to less than 90°) with respect to first surface 22.

According to an embodiment, interfacial layer 20 is disposed on first layer 22. Interfacial layer 20 can include an oxide such as an oxide that includes an element from first layer 22, e.g., an oxide of the semiconductor (also referred to herein as a semiconductor oxide). In an embodiment, first layer 22 includes Si, and interfacial layer 20 includes silicon dioxide ($SiO_2$). Other materials for interfacial layer 20 include gallium oxide ($GaO_3$), aluminum oxide ($Al_2O_3$), or alloys thereof, oxides of compounds from Groups III and V or alloys thereof, and the like. Exemplary oxides in interfacial layer 20 also include ZnO, $HfO_2$, $SnO_2$, $In_2O_3$, $Zn_2SnO_4$, $Ga_2O_3$, $Al_2O_3$, and the like. In an embodiment, interfacial layer 20 is a product of oxidation of a portion of first layer 20 (or a top-most layer of a substrate from which first 20 is made) to produce the semiconductor oxide. According to one embodiment, the oxide is a product of rapid thermal oxidation (RTO) of first layer 20 (referred to herein as an "RTO oxide") so that the oxide (interfacial layer 20) is derived from first layer 22. In another embodiment, the oxide is a product of low temperature oxidation (LTO) of first layer 22 to produce an oxide (referred to herein as an "LTO oxide") having different properties than the RTO oxide. In a further embodiment, the oxide is a product of depositing the oxide on first layer 22, which can involve oxidation of first layer 22. In a certain embodiment, interfacial layer 20 includes RTO $SiO_2$ as the oxide, which is a product of rapid thermal oxidation of first layer 22 that includes Si. In some embodiments, interfacial layer 20 includes a semiconductor oxide, a ceramic (e.g., $ZrO_2$, $Al_2O_3$, SiC, $Si_3N_4$, BN, $BaTiO_3$, and the like), a glass, or a combination comprising at least one of foregoing.

Nanotube 12 can include a material recited for interfacial layer 20. In some embodiments, nanotube 12 and interfacial layer 20 are a substantially same material. In other embodiments, nanotube 12 and interfacial layer 20 are a different material.

In an embodiment, nanotube 12 can be functionalized such that inner wall 34 of nanotube 12 includes a functional group attached to the semiconductor oxide. In some embodiments, the functional group can be a hydrophilic moiety, e.g., having a hydrophilicity greater than that of glycine in accordance with hydrophilicity values published in Hopp and Woods, "Prediction of protein antigenic determinants from amino acid sequences," 78 Proc. Natl. Acad. Sci. U.S.A., 3824 (1981). In some embodiments, the functional group can be a hydrophobic moiety, e.g., having a hydrophilicity less than that of glycine.

Figure 14:
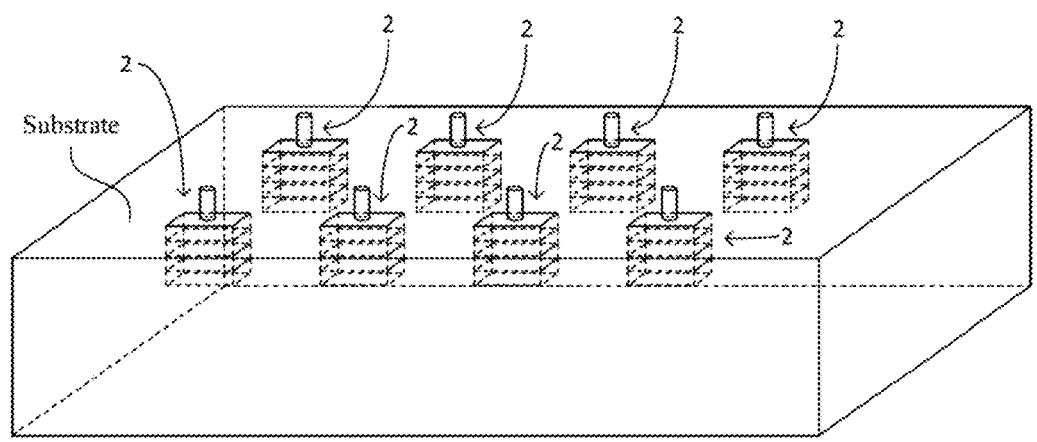
FIG. 14 shows an array of single molecule filters.
Figure 15:
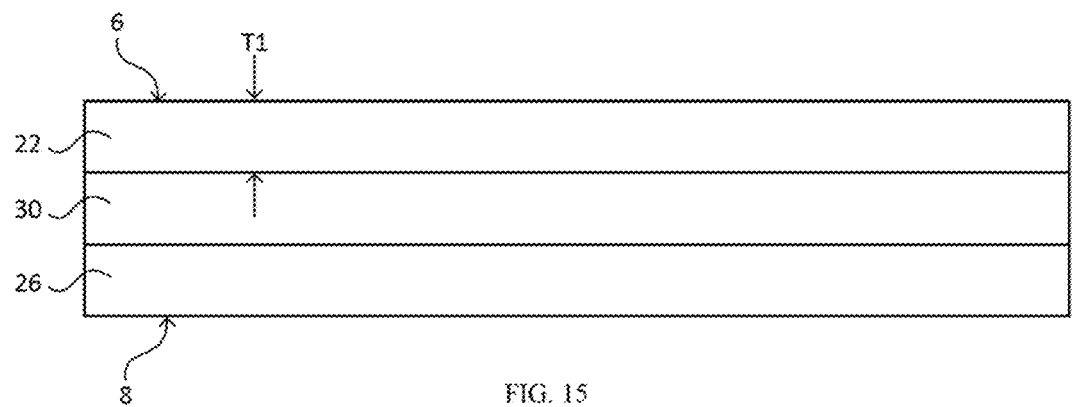
FIG. 15 shows a substrate.
Figure 16:
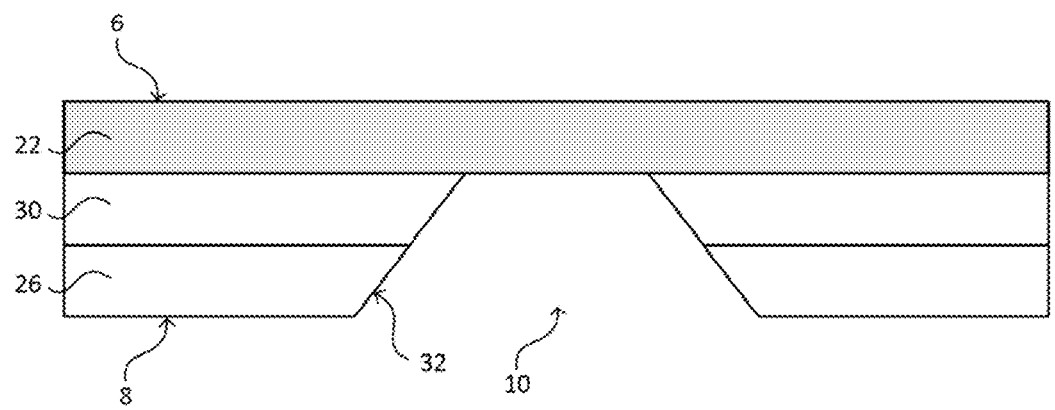
FIG. 16 shows a membrane aperture in a substrate.
Figure 17:
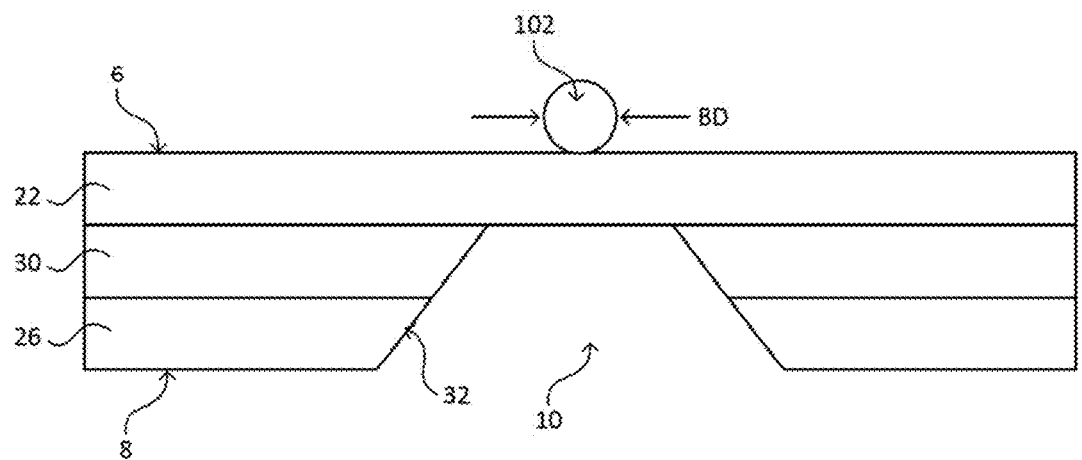
FIG. 17 shows a catalyst disposed on a first surface.
Figure 18:
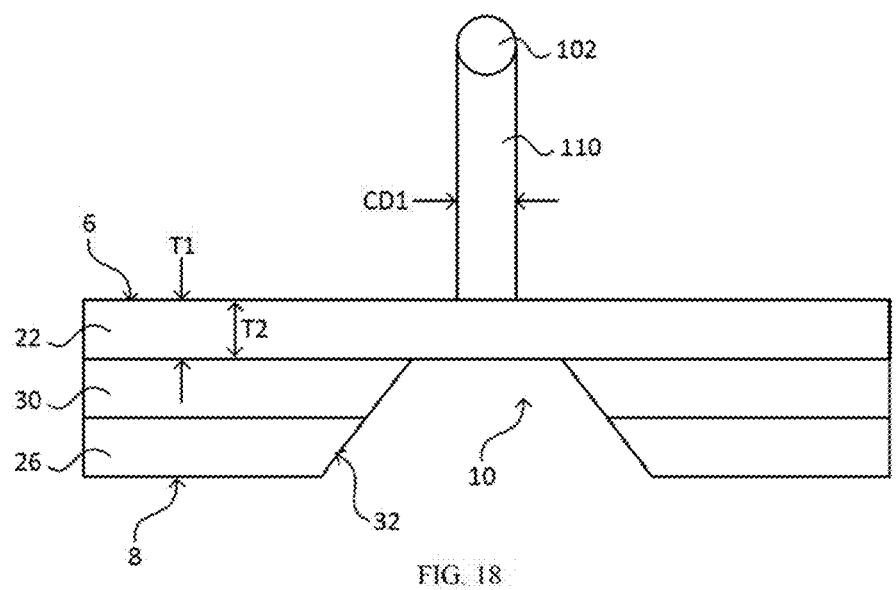
FIG. 18 shows a nanocolumn interposed between a catalyst and a first surface.
Figure 19:
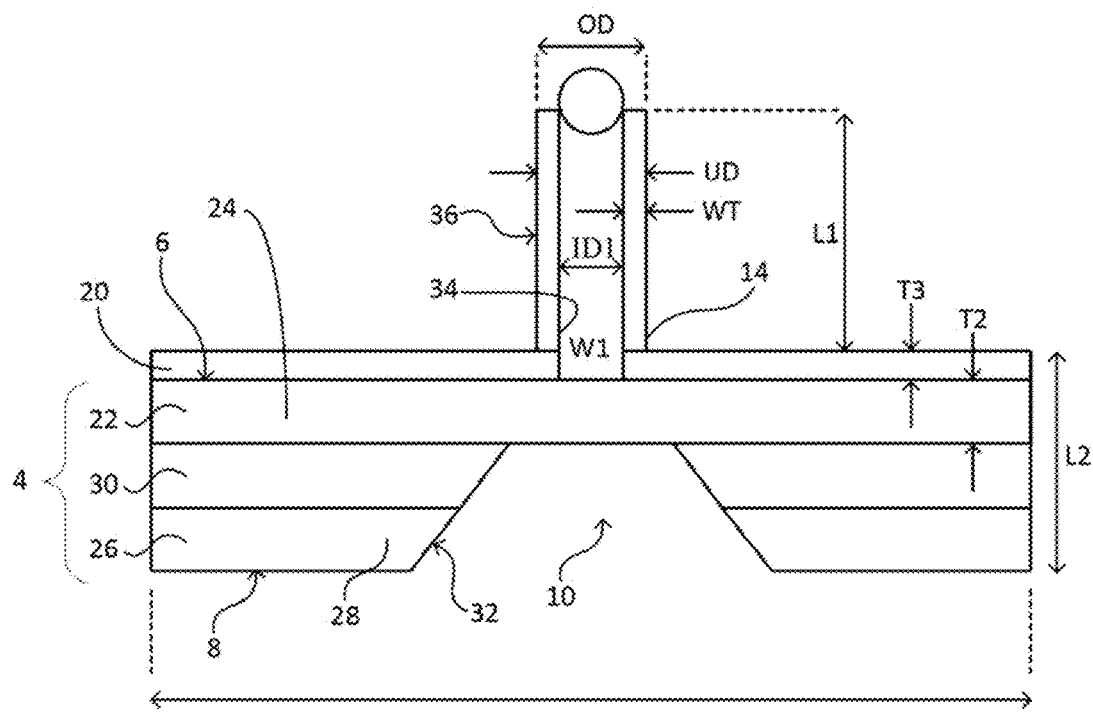
FIG. 19 shows a nanotube surroundingly disposed on a nanocolumn and disposed on an interfacial layer.
Figure 20:
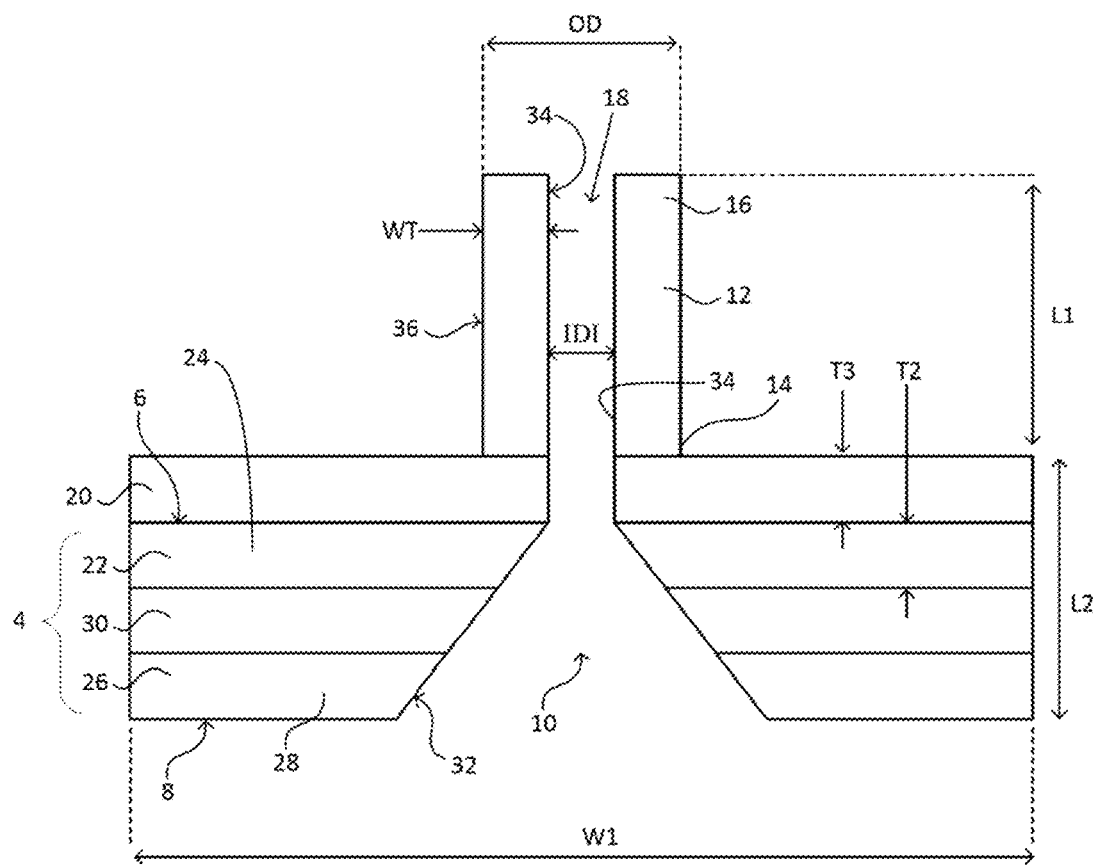
FIG. 20 shows a nanotube disposed on a membrane.
Figure 21:
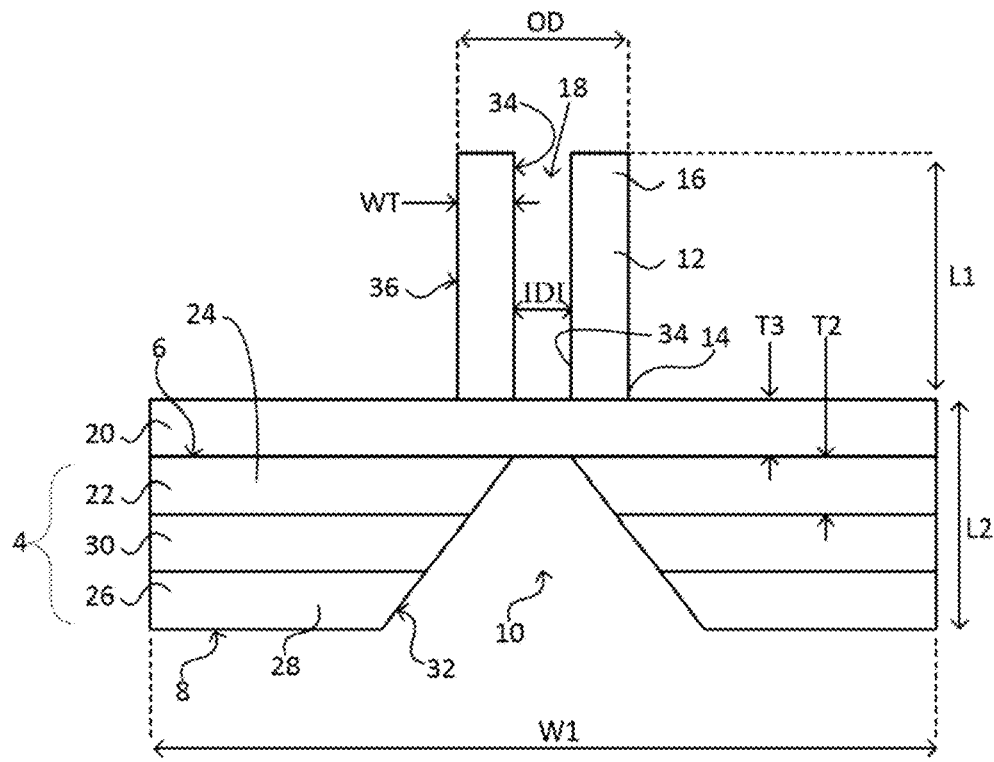
FIG. 21 shows a nanotube disposed on an interfacial layer.
Figure 22:
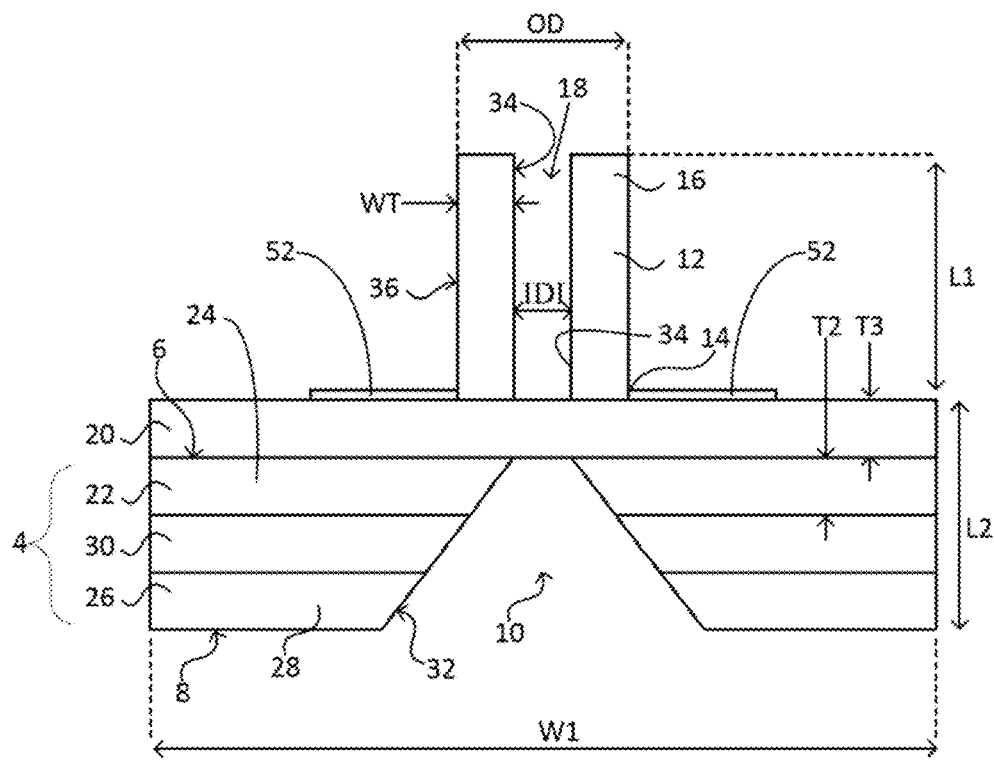
FIG. 22 shows an active element surroundingly disposed around a nanotube and disposed on an interfacial layer.
Figure 23:
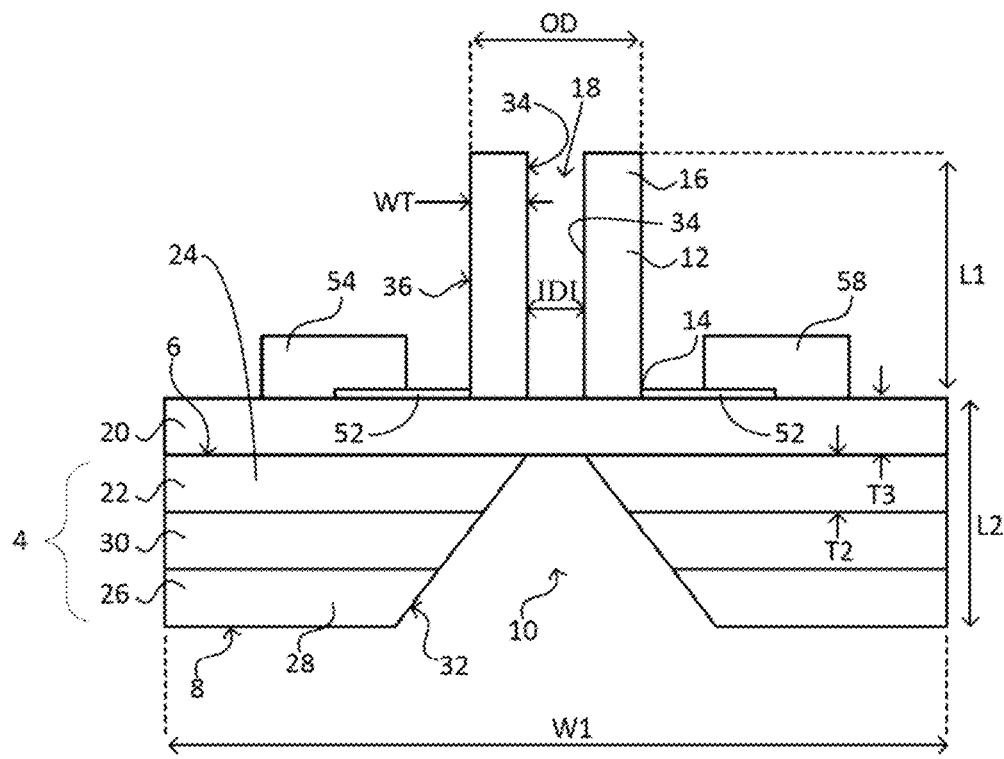
FIG. 23 shows a source electrode and a drain electrode disposed on an active element.
Figure 24:
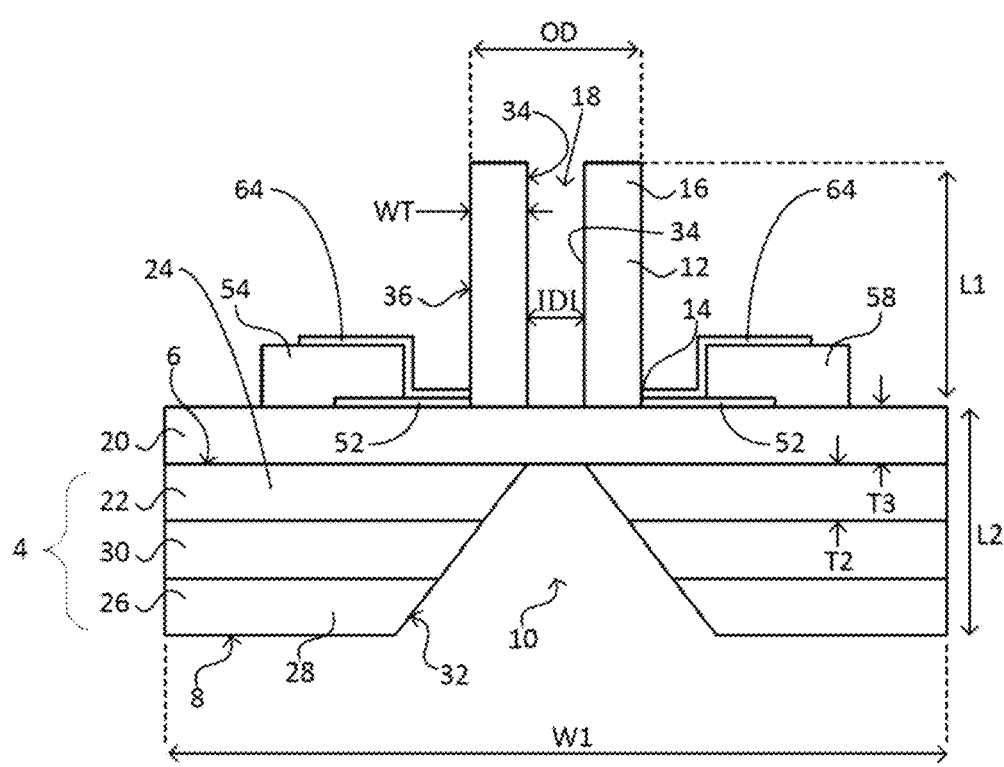
FIG. 24 shows a gate dielectric disposed on a source electrode and a drain electrode.
Figure 25:
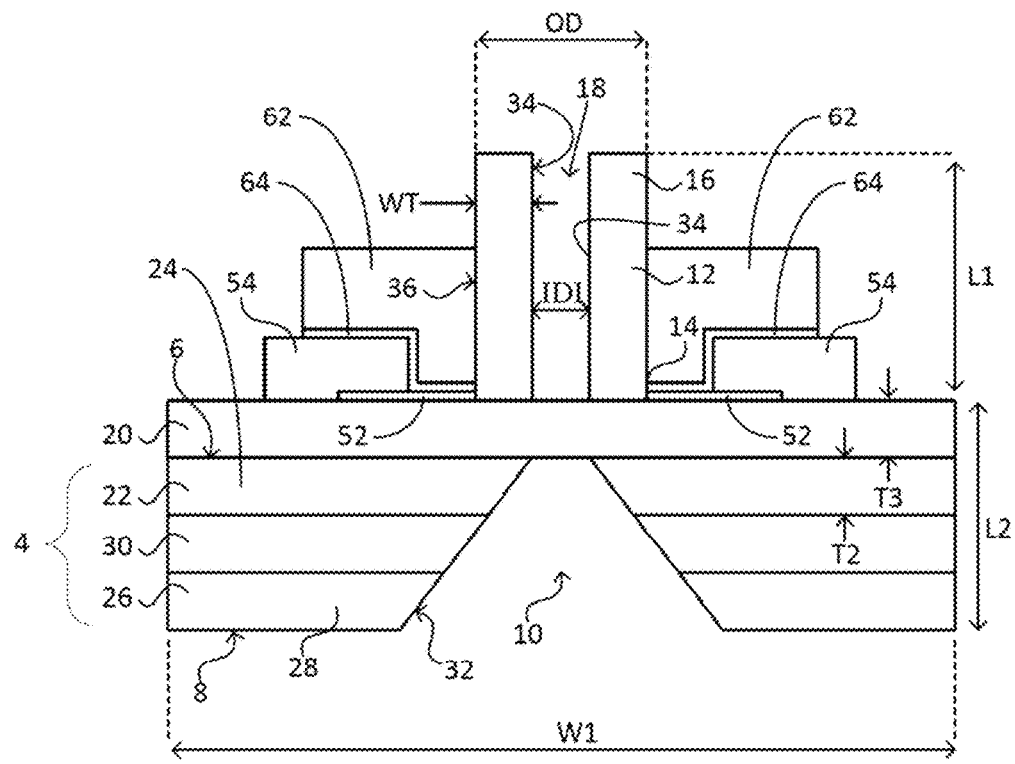
FIG. 25 shows gate electrode disposed on a gate dielectric.
Figure 26:
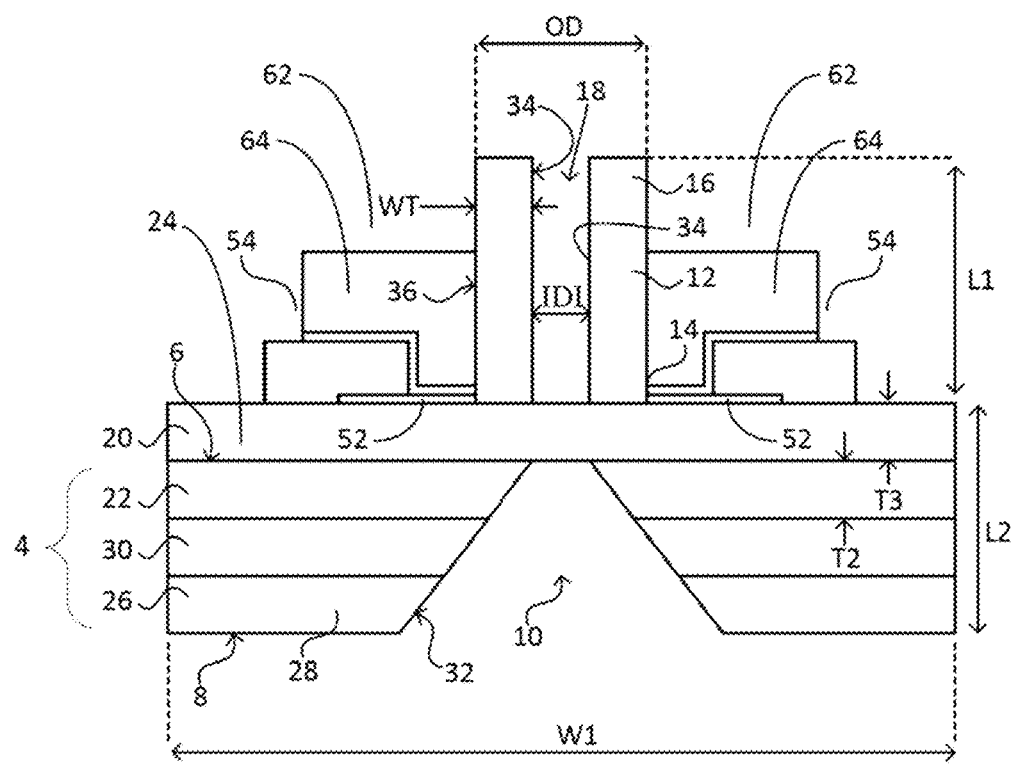
FIG. 26 shows a single molecule electrograph.

Exemplary functional groups include carboxy (e.g., carboxylic acid groups), epoxy, ether, ketone, amine, hydroxy, alkoxy, alkyl, aryl, aralkyl, alkaryl, lactone, functionalized polymeric or oligomeric groups, and the like. In an embodiment, with reference to FIG. 14, a plurality of nanotubes 12 can be included membrane 4, and nanotubes 12 can include a combination of functionalized nanotubes 12 and non-functionalized nanotubes 12. The plurality of nanotubes can be arranged, e.g., in an array format.

According to an embodiment, nanotubes 12 are functionalized to include a functional group that is hydrophilic, hydrophobic, oxophilic, lipophilic, or oleophilic to provide selectively of communication of species or conformations or single molecule 78 through tubular aperture 18.

In an exemplary embodiment, nanotube 12 is functionalized, e.g., by amination to include amine groups, where amination may be accomplished by nitration followed by reduction, or by nucleophilic substitution of a leaving group by an amine, substituted amine, or protected amine, followed by deprotection as necessary. In another embodiment, nanotube 12 is functionalized by oxidative methods to produce an epoxy, hydroxy group, or glycol group using a peroxide, or by cleavage of a double bond by for example a metal mediated oxidation such as a permanganate oxidation to form ketone, aldehyde, or carboxylic acid functional groups.

Where the functional groups are alkyl, aryl, aralkyl, alkaryl, functionalized polymeric or oligomeric groups, or a combination of these groups, the functional groups can be attached to inner wall 34 of nanotube 12 through intermediate functional groups (e.g., carboxy, amino) or directly to inner wall 34 by: a carbon-carbon bond without intervening heteroatoms, to provide greater thermal and/or chemical stability to inner wall, as well as a more efficient synthetic process in fewer steps; by a carbon-oxygen bond (where inner wall 34 includes an oxygen-containing functional group such as hydroxy or carboxylic acid); or by a carbon-nitrogen bond (where inner wall 34 includes a nitrogen-containing functional group such as amine or amide). In an embodiment, inner wall 34 is functionalized by metal mediated reaction with a C6-30 aryl or C7-30 aralkyl halide (F, Cl, Br, I) in a carbon-carbon bond forming step, such as by a palladium-mediated reaction such as the Stille reaction, Suzuki coupling, or diazo coupling, or by an organocopper coupling reaction.

In another embodiment, inner wall 34 of nanotube 12 is directly metallated by reaction with, e.g., an alkali metal such as lithium, sodium, or potassium, followed by reaction with a C1-30 alkyl or C7-30 alkaryl compound with a leaving group such as a halide (Cl, Br, I) or other leaving group (e.g., tosylate, mesylate, etc.) in a carbon-carbon bond forming step. The aryl or aralkyl halide, or the alkyl or alkaryl compound, may be substituted with a functional group such as hydroxy, carboxy, ether, or the like. Exemplary groups include, for example, hydroxy groups, carboxylic acid groups, alkyl groups such as methyl, ethyl, propyl, butyl, pentyl, hexyl, octyl, dodecyl, octadecyl, and the like; aryl groups including phenyl and hydroxyphenyl; alkaryl groups such as benzyl groups attached via the aryl portion, such as in a 4-methylphenyl, 4-hydroxymethylphenyl, or 4-(2-hydroxyethyl)phenyl (also referred to as a phenethyl-alcohol) group, or the like, or aralkyl groups attached at the benzylic (alkyl) position such as found in a phenylmethyl or 4-hydroxyphenyl methyl group, at the 2-position in a phenethyl or 4-hydroxyphenethyl group, or the like. In an exemplary embodiment, the functionalized inner wall 34 includes silicon dioxide functionalized with glycines or similar species to produce inner wall 34 of nanotube 12 that is hydrophilic.

In an embodiment, inner wall 34 has an anionic functional group such as a sulfonic acid group, carboxyl group, phosphoric acid group, phosphorous acid group, phosphinic acid group, or a combination thereof. In some embodiments, inner wall 34 is functionalized with an anionic group, and inner wall 34 also includes a cationic functional group, wherein a number of cationic functional groups is larger than a number of anionic functional groups such that inner wall 34 has a positive charge. In another embodiment, inner wall 34 has a basic or cationic functional group. The basic functional group is, e.g., a primary amino group, secondary amino group, tertiary amino group, or a combination thereof. The cationic functional group is, e.g., a quaternary ammonium group, quaternary phosphonium group, tertiary sulfonium group, alkyl pyridinium group, or a combination thereof. In an embodiment, inner wall 34 has a cationic functional group including a primary amine ($-NH_2$), secondary amine ($-NHR$, where R may be, for example, an alkyl or aryl group), tertiary amine ($-NR_2$, where each R may be the same or different group, for example an alkyl or aryl group), or combination thereof. Examples of such functional groups include aminoethyl, dimethylaminoethyl, diethylaminoethyl, and similar groups.

In an embodiment, nanotube 12 is made by oxidizing nanocolumn 110 and includes an oxide of a material included in nanocolumn 110. Nanocolumn 110 is disposed on a surface a first layer 22 and can include a material recited for first layer 22 such that nanotube 12 includes an oxide of such material.

In single molecule electrograph 50, transistor 66 includes gate electrode 62, source electrode 54, and drain electrode 58 that independently include an electrically conductive material and provide injection of electrons in other components of transistor 66. The electrically conductive material has a high electrical conductivity and efficiently communicates electrons therethrough. Exemplary electrically conductive materials include graphite, graphene, carbon fibers, metallic nanoparticles (e.g., carbon nanotubes that metallic-(n,m)-nanotubes), metal, and the like. In an embodiment, the electrically conductive material includes a transition metal, alkaline earth metal, alkali metal, rare earth metal, metal carbide, metal oxide, metal sulfide, non-metals (e.g., graphene, carbon nanotubes, carbon black, and the like), or a combination thereof. Exemplary metals include Zr, Hf, Ti, V, Cr, Mn, Fe, Co, Ni, Cu, Zn, Nb, Mo, Tc, Ru, Rh, Pd, Ag, Cd, Ta, W, Re, Os, Ir, Pt, Au, Li, Na, K, Be, Mg, Ca, Sr, Ba, Gd, and the like. According to an embodiment, gate electrode 62, source electrode 54, and drain electrode 58 independently include Au, Ti, and the like.

Active element 52 of transistor 66 communicates electrons between source electrode 54 and drain electrode 58 and includes material selected for high efficiency communication of the electrons to form the drain current in transistor 66. Exemplary materials for active element 52 include a transition metal dichalcogenide and similar species such as molybdenum disulfide, gallium nitride, silicon, and the like.

Gate dielectric 64 is interposed between source electrode 54 and gate electrode 62 and also is interposed between drain electrode 58 and source electrode 54 to insulate electrically these elements from one another. Gate dielectric 64 can be a material that is a high-k dielectric material such as, e.g., silicon dioxide, hafnium dioxide, aluminum oxide, and the like.

Composition 76 can be disposed proximate to single molecule filter 2 or single molecule electrograph 50 such that single molecule 78 disposed in composition can be communicated through tubular aperture 18 of nanotube 12. In addition to single molecule 78, composition 76 also can include a fluid in which single molecule 78 is disposed. The fluid can include a solvent, a plurality of charged species including an ionic liquid, a plurality of ions, charged buffer molecules, or a combination thereof.

Single molecule 78 can be a molecule that has a fixed surface charge, an adsorbed charge, ionizable (titratable) charge, or the like. Exemplary single molecules 78 include biomolecules (e.g., a protein, nucleic acid, small molecule neurotransmitters, hormones, and the like), synthetic polymers (e.g., poly(ethylene glycol), and the like. In a particular embodiment, single molecule 78 includes a protein. The protein can be in its native conformation or denatured partially or fully. Exemplary proteins include stroke markers, cardiac markers, antigens, antibodies, and the like.

Exemplary charged particles include positively charged particles, negatively charged particles, or zwitterions such as protons, hydroxide, alkali metal cations, halogen anions, carbonates, alcoholates, sulfonates, sulfates, phosphates, phosphonates, $BF_4^-$, $PF_6^-$, $(CF_3SO_2)_2N^-$, $CF_3SO_3^-$, $CF_3CO_2^-$, $AsF_6^-$, $SbF_6^-$, $AlCl_4^-$, $NbF_6^-$, $HSO_4^-$, $ClO_4^-$, $CH_3SO_3^-$, $CF_3SO_3^-$, $(CF_3SO_2)_2N^-$, $Cr^-$, N-methylpyrrolidiinum, pyrrolidinium, 1-ethylimidazolium, 1-ethyl-3-methylimidazolium, 2-methyl-1-pyrrolinium, N-butylpyridinium, and the like. Further exemplary charged species include pyrophosphates, hexametaphosphates, ethylenediaminetetraacetates, N-(2-hydroxyethyl)-ethylenediaminetriacetates, nitrilotriacetates, N-(2-hydroxyethyl)-nitrilodiacetates, phytates, ethane-1-hydroxy-1,1-diphosphonates, methylene diphosphonates, ethylidene, isopropylidene, benzylmethylidene and chloromethylidene diphosphonates, salts of polymers of itaconic acid, aconitic acid, maleic acid, mesaconic acid, fumaric acid, methylene malonic acid and citraconic acid and copolymers with themselves and ethylene, and mixtures thereof. Exemplary cations sodium, potassium, ammonium, triethanol ammonium, diethanol ammonium and monoethanol ammonium cations, and the like.

According to an embodiment, the charged particle is the ionic liquid that has a cation that includes imidazolium, pyrazolium, pyridinium, ammonium, pyrrolidinium, sulfonium, phosphonium, morpholinium, derivatives thereof, or a combination comprising at least one of the foregoing.

The anion of the ionic liquid is not particularly limited as long as the anion does not interfere with communication of single molecule 78 through tubular aperture 18. Exemplary anions include halide (e.g., fluoride, chloride, bromide, iodide), tetrachloroaluminate ($AlCl_4^-$), hexafluorophosphate ($PF_6^-$), hexafluoroarsenate ($AsF_6^-$), tetrafluroborate ($BF_4^-$), triflate ($CF_3SO_3^-$), mesylate ($CH_3SO_3^-$), dicyanamide ($(NC)_2N^-$), thiocyanate ($SCN^-$), alkylsulfate ($ROSO_3^-$, where R is a halogentated or non-halogenated linear or branched alkyl group, e.g., $CH_3CH_2OSO_3^-$), tosylate, bis(trifluoromethyl-sulfonyl)imide, alkyl sulfate ($ROSO_3^-$, where R is a halogentated or non-halogenated linear or branched alkyl group, e.g., $CF_2HCH_2OSO_3^-$), alkyl carbonate ($ROCO_2^-$, where R is a halogentated or non-halogenated linear or branched alkyl group), or a combination thereof.

Exemplary ionic liquids include imidazolium salts with oligo(ethylene glycol) groups such as 1-ethyl-3-(2-methoxyethoxy)methyl)-1H-imidazol-3-ium bis(trifluoromethanesulfonyl)imide; 1-ethyl-3-((2-(2-methoxyethoxy)ethoxy)methyl)-1H-imidazol-3-ium bis(trifluoromethanesulfonyl)imide; 3-2,5,8,11-tetraoxadodecyl-1-ethyl-1H-imidazol-3-ium bis(trifluoromethanesulfonyl)imide; 1-ethyl-3-((2-methoxyethoxy)methyl)-1H-imidazol-3-ium bis(fluoromethanesulfonyl)imide; 1-ethyl-3-((2-(2-methoxyethoxy)ethoxy)methyl)-1H-imidazol-3-ium bis(fluoromethanesulfonyl)imide; 3-2,5,8,11-tetraoxadodecyl-1-ethyl-1H-imidazol-3-ium bis(fluoromethanesulfonyl)imide; 1-ethyl-3-((2-methoxyethoxy)methyl)-1H-imidazol-3-ium bis(oxalato)borate; 1-ethyl-3-((2-(2-methoxyethoxy)ethoxy)methyl)-1H-imidazol-3-ium bis(oxalato)borate; 3-2,5,8,11-tetraoxadodecyl-1-ethyl-1H-imidazol-3-ium bis(oxalato)borate; 1-ethyl-3-((2-methoxyethoxy)methyl)-1H-imidazol-3-ium hexafluorophosphate; 1-ethyl-3-((2-(2-methoxyethoxy)ethoxy)methyl)-1H-imidazol-3-ium hexafluorophosphate, 3-2,5,8,11-tetraoxadodecyl-1-ethyl-1H-imidazol-3-ium hexafluorophosphate, and the like.

Further exemplary ionic liquids include imidazolium salts with siloxane groups such as 1-ethyl-3-(methylenepentamethyldisiloxane)-1H-imidazol-3-ium bis(trifluoromethanesulfonyl)imide; 1-ethyl-3-(methyleneheptamethyltrisiloxane)-1H-imidazol-3-ium bis(trifluoromethanesulfonyl)imide; 1-ethyl-3-(methyleneoctamethyltetrasiloxane)-1H-imidazol-3-ium bis(trifluoromethanesulfonyl)imide; 1-ethyl-3-(methylenepentamethyldisiloxane)-1H-imidazol-3-ium bis(oxalato)borate; 1-ethyl-3-(methyleneheptamethyltrisiloxane)-1H-imidazol-3-ium bis(oxalato)borate; 1-ethyl-3-(methyleneoctamethyltetrasiloxane)-1H-imidazol-3-ium bis(oxalato)borate; 1-ethyl-3-(methylenepentamethyldisiloxane)-1H-imidazol-3-ium bis(fluoromethanesulfonyl)imide; 1-ethyl-3-(methyleneheptamethyltrisiloxane)-1H-imidazol-3-ium bis(fluoromethanesulfonyl)imide; 1-ethyl-3-(methyleneoctamethyltetrasiloxane)-1H-imidazol-3-ium bis(fluoromethanesulfonyl)imide; 1-ethyl-3-(methylenepentamethyldisiloxane)-1H-imidazol-3-ium hexafluorophosphate; 1-ethyl-3-(methyleneheptamethyltrisiloxane)-1H-imidazol-3-ium hexafluorophosphate; 1-ethyl-3-(methyleneoctamethyltetrasiloxane)-1H-imidazol-3-ium hexafluorophosphate, and the like.

Exemplary ionic liquids include but are not limited to imidazolium salts with sulfone groups such as 1-ethyl-3-(2-(methylsulfonyl)ethyl)-1H-imidazol-3-ium bis(trifluoromethanesulfonyl)imide; 1-ethyl-3-(2-(ethylsulfonyl)ethyl)-1H-imidazol-3-ium bis(trifluoromethanesulfonyl)imide; 1-ethyl-3-(2-(propylsulfonyl)ethyl)-1H-imidazol-3-ium bis(trifluoromethanesulfonyl)imide; 1-ethyl-3-(2-(butylsulfonyl)ethyl)-1H-imidazol-3-ium bis(trifluoromethanesulfonyl)imide; 1-ethyl-3-(2-(methylsulfonyl)ethyl)-1H-imidazol-3-ium bis(oxalato)borate; 1-ethyl-3-(2-(ethylsulfonyl)ethyl)-1H-imidazol-3-ium bis(oxalato)borate; 1-ethyl-3-(2-(propylsulfonyl)ethyl)-1H-imidazol-3-ium bis(oxalato)borate; 1-ethyl-3-(2-(butylsulfonyl)ethyl)-1H-imidazol-3-ium bis(oxalato)borate; 1-ethyl-3-(2-(methylsulfonyl)ethyl)-1H-imidazol-3-ium bis(fluoromethanesulfonyl)imide; 1-ethyl-3-(2-(ethylsulfonyl)ethyl)-1H-imidazol-3-ium bis(fluoromethanesulfonyl)imide; 1-ethyl-3-(2-(propylsulfonyl)ethyl)-1H-imidazol-3-ium bis(fluoromethanesulfonyl)imide; 1-ethyl-3-(2-(butylsulfonyl)ethyl)-1H-imidazol-3-ium bis(fluoromethanesulfonyl)

imide; 1-ethyl-3-(2-(methylsulfonyl)ethyl)-1H-imidazol-3-ium hexafluorophosphate; 1-ethyl-3-(2-(ethylsulfonyl)ethyl)-1H-imidazol-3-ium hexafluorophosphate; 1-ethyl-3-(2-(propylsulfonyl)ethyl)-1H-imidazol-3-ium hexafluorophosphate; 1-ethyl-3(2-(butylsulfonyl)ethyl)-1H-imidazol-3-ium hexikluorophosphate, and the like.

Exemplary ionic liquids also include imidazolium salts with carbonate groups such as 1-ethyl-3-((2-oxo-1,3-dioxolan-4-yl)methyl)-1H-imidazol-3-ium bis(trifluoromethanesulfonyl)imide; 1-ethyl-3-((2-oxo-1,3-dioxolan-4-yl)ethyl)-1H-imidazol-3-ium bis(trifluoromethanesulfonyl)imide; 1-ethyl-3-((2-oxo-1,3-dioxolan-4-yl)propyl)-1H-imidazol-3-ium bis(trifluoromethanesulfonyl)imide; 1-ethyl-3-((2-oxo-1,3-dioxolan-4-yl)methyl)-1H-imidazol-3-ium bis(oxalato)borate; 1-ethyl-3-((2-oxo-1,3-dioxolan-4-yl)ethyl)-1H-imidazol-3-ium bis(oxalato)borate; 1-ethyl-3-((2-oxo-1,3-dioxolan-4-yl)propyl)-1H-imidazol-3-ium bis(oxalato)borate; 1-ethyl-3-((2-oxo-1,3-dioxolan-4-yl)methyl)-1H-imidazol-3-ium bis(fluoromethanesulfonyl)imide; 1-ethyl-3-((2-oxo-1,3-dioxolan-4-yl)ethyl)-1H-imidazol-3-ium bis(fluoromethanesulfonyl)imide; 1-ethyl-3-((2-oxo-1,3-dioxolan-4-yl)propyl)-1H-imidazol-3-ium bis(fluoromethanesulfonyl)imide; 1-ethyl-3-((2-oxo-1,3-dioxolan-4-yl)methyl)-1H-imidazol-3-ium hexafluorophosphate; 1-ethyl-3-((2-oxo-1,3-dioxolan-4-yl)ethyl)-1H-imidazol-3-ium hexafluorophosphate; 1-ethyl-3-((2-oxo-1,3-dioxolan-4-yl)propyl)-1H-imidazol-3-ium hexafluorophosphate, and the like.

Exemplary ionic liquids include but are not limited to phosphonium salts with oligo(ethylene glycol) groups such as triethyl((2-methoxyethoxy)methyl)phosphonium bis(trifluoromethylsulfonyl)imide; triethyl((2-(2-methoxyethoxy)ethoxy)methyl)phosphonium bis(trifluoromethylsulfonyl)imide; triethyl((2-(2-(2-methoxyethoxy)ethoxy)ethoxy)methyl)phosphonium bis(trifluoromethylsulfonyl)imide; triethyl((2-methoxyethoxy)methyl)phosphonium bis(fluoromethylsulfonyl)imide; triethyl((2-(2-methoxyethoxy)ethoxy)methyl)phosphonium bis(fluoromethylsulfonyl)imide; triethyl((2-(2-(2-methoxyethoxy)ethoxy)ethoxy)methyl)phosphonium bis(fluoromethylsulfonyl)imide; triethyl((2-methoxyethoxy)methyl)phosphonium bis(oxalato)borate; triethyl((2-(2-methoxyethoxy)ethoxy)methyl)phosphonium bis(oxalato)borate; triethyl((2-(2-(2-methoxyethoxy)ethoxy)ethoxy)methyl)phosphonium bis(oxalato)borate; triethyl((2-methoxyethoxy)methyl)phosphonium hexafluorophosphate; triethyl((2-(2-methoxyethoxy)ethoxy)methyl)phosphonium hexafluorophosphate; triethyl((2-(2-(2-methoxyethoxy)ethoxy)ethoxy)methyl)phosphonium hexafluorophosphate, and the like.

Exemplary ionic liquids further include phosphonium salts with siloxane groups such as triethyl-(methylenepentamethyldisiloxane)phosphonium bis(trifluoromethylsulfonyl)imide; triethyl-(methyleneheptamethyltrisiloxane)phosphonium bis(trifluoromethylsulfonyl)imide; triethyl-(methyleneoctamethyltetrasiloxane)phosphonium bis(trifluoromethylsulfonyl)imide; triethyl-(methylenepentamethyldisiloxane)phosphonium bis(fluoromethylsulfonyl)imide; triethyl-(methyleneheptamethyltrisiloxane)phosphonium bis(fluoromethylsulfonyl)imide; triethyl-(methyleneoctamethyltetrasiloxane)phosphonium bis(fluoromethylsulfonyl)imide; triethyl-(methylenepentamethyldisiloxane)phosphonium bis(oxalato)borate; triethyl-(methyleneheptamethyltrisiloxane)phosphonium bis(oxalato)borate; triethyl-(methyleneoctamethyltetrasiloxane)phosphonium bis(oxalato)borate; triethyl-(methylenepentamethyldisiloxane)phosphonium hexafluorophosphate; triethyl-(methyleneheptamethyltrisiloxane)phosphonium hexafluorophosphate; triethyl-(methyleneoctamethyltetrasiloxane)phosphonium hexafluorophosphate, and the like.

Exemplary ionic liquids include but are not limited to phosphonium salts with sulfone groups such as triethyl-(2-(methylsulfonyl)ethyl)phosphonium bis(trifluoromethylsulfonyl)imide; triethyl-(2-(ethylsulfonyl)ethyl)phosphonium bis(trifluoromethylsulfonyl)imide; triethyl-(2-(propylsulfonyl)ethyl)phosphonium bis(trifluoromethylsulfonyl)imide; triethyl-(2-(butyl sulfonyl)ethyl)phosphonium bis(trifluoromethylsulfonyl)imide; triethyl-(2-(methylsulfonyl)ethyl)phosphonium bis(fluoromethylsulfonyl)imide; triethyl-(2-(ethylsulfonyl)ethyl)phosphonium bis(fluoromethylsulfonyl)imide; triethyl-(2-(propylsulfonyl)ethyl)phosphonium bis(fluoromethylsulfonyl)imide; triethyl-(2-(butylsulfonyl)ethyl)phosphonium bis(fluoromethylsulfonyl)imide; triethyl-(2-(methylsulfonyl)ethyl)phosphonium bis(oxalato)borate; triethyl-(2-(ethylsulfonyl)ethyl)phosphonium bis(oxalato)borate; triethyl-(2-(propylsulfonyl)ethyl)phosphonium bis(oxalato)borate; triethyl-(2-(butylsulfonyl)ethyl)phosphonium bis(oxalato)borate; triethyl-(2-(methylsulfonyl)ethyl)phosphonium hexafluorophosphate; triethyl-(2-(ethylsulfonyl)ethyl)phosphonium hexafluorophosphate; triethyl-(2-(propylsulfonyl)ethyl)phosphonium hexafluorophosphate; triethyl-(2-(butylsulfonyl)ethyl)phosphonium hexafluorophosphate, and the like.

Additional exemplary ionic liquids include phosphonium salts with carbonate groups such as triethyl-3-((2-oxo-1,3-dioxolan-4-yl)methyl)phosphonium bis(trifluoromethylsulfonyl)imide; triethyl-3-((2-oxo-1,3-dioxolan-4-yl)ethyl)phosphonium bis(trifluoromethylsulfonyl)imide; triethyl-3-((2-oxo-1,3-dioxolan-4-yl)propyl)phosphonium bis(trifluoromethylsulfonyl)imide; triethyl-3-((2-oxo-1,3-dioxolan-4-yl)methyl)phosphonium bis(fluoromethylsulfonyl)imide; triethyl-3-((2-oxo-1,3-dioxolan-4-yl)ethyl)phosphonium bis(fluoromethylsulfonyl)imide; triethyl-3-((2-oxo-1,3-dioxolan-4-yl)propyl)phosphonium bis(fluoromethylsulfonyl)imide; triethyl-3-((2-oxo-1,3-dioxolan-4-yl)methyl)phosphonium bis(oxalato)borate; triethyl-3-((2-oxo-1,3-dioxolan-4-yl)ethyl)phosphonium bis(oxalato)borate; triethyl-3-((2-oxo-1,3-dioxolan-4-yl)propyl)phosphonium bis(oxalato)borate; triethyl-3-((2-oxo-1,3-dioxolan-4-yl)methyl)phosphonium hexafluorophosphate; triethyl-3-((2-oxo-1,3-dioxolan-4-yl)ethyl)phosphonium hexafluorophosphate; triethyl-3-((2-oxo-1,3-dioxolan-4-yl)propyl)phosphonium hexafluorophosphate, and the like.

Examples of the ionic liquid include but are not limited to 3-ethyl-1-vinylimidazlium tetrafluoroborate, 1-methyl-3-vinylimidazolium methyl carbonate, 1-isobutenyl-3-methylimidazolium tetrafluoroborate, 1-allyl-3-methylimidazolium bis(trifluoromethylsulfonyl)imide, 1-allyl-3-methylimidazolium bromide, 1,3-bis(cyanomethyl)imidazolium bis(trifluoromethylsulfonyl)imide, 1-ethyl-nicotinic acid ethyl ester ethylsulfate, 1-butyl-nicotinic acid butyl ester bis[(trifluoromethyl)sulfonyl]imide, 1-(3-cyanopropyl)-3-methylimidazolium bis(trifluoromethylsulfonyl)amide, 1,3-diallylimidazolium bis(trifluoromethylsulfonyl)imide, ethyl-dimethyl-(cyanomethyl)ammonium bis(trifluoromethylsulfonyl)imide, 3-[4-(acryloyloxy)butyl]-1-methyl-1H-imidazol-3-ium hexafluorophosphate, 1-methyl-3-{3-[(2-methylacryloyl)oxy]propyl}-1H-imidazol-3-ium bromide, and 3-ethenyl-1-ethyl-1H-imidazol-3-ium bis(trifluoromethylsulfonyl)imide. According to an embodiment, the ionic liquid that is used as a solvent includes aluminum chloride-1-ethyl-3-methylimidazolium chloride (AlCl₃-EMIC); aluminum chloride-N-(n-butyl)pyridinium chloride (AlCl₃-BPC); 1-butyl-1-methylpyrrolidinium bis(trifluoromethylsulfonyl)amide (BMPTFSA); 1-butyl-3-methylimidazolium chloride; 1-butyl-3-methylimidazolium bis(trifluoromethylsulfonyl)imide; 1-butyl-3-methylimidazolium dicyanamide; and the like.

In an embodiment, composition 76 further includes a buffer, a surfactant, the solvent, or a combination thereof. The buffer is included to control the pH of composition 76 or to mediate the pH or the conformation of single molecule 78. Exemplary buffers are alkali salts of weak acids such as formic acid, acetic acid, citric acid, and the like; sulfonic acids; boric acid; and the like. In an embodiment, composition 76 is aqueous and has a pH that is neutral (physiologically neutral with respect, e.g., to a protein), acidic, or basic. A pH control agent can be added such as a weak acid, weak base, strong acid, strong base, or combination thereof to control a pH of composition 76 to a selected value that is acidic, neutral, or basic.

The surfactant is included in composition 76, e.g., to disperse single molecule 78 in composition 76. Exemplary surfactants include fatty acids of up to 22 carbon atoms such as stearic acids and esters and polyesters thereof, poly (alkylene glycols) such as poly(ethylene oxide), poly(propylene oxide), and block and random poly(ethylene oxide-propylene oxide) copolymers such as those marketed under the trademark PLURONIC by BASF. Surfactants also include polysiloxanes, such as homopolymers and copolymers of poly(dimethylsiloxane), including those having functionalized end groups, and the like. Additional surfactants include those having a polymeric dispersant having poly(alkylene glycol) side chains, fatty acids, or fluorinated groups such as perfluorinated $C_{1-4}$ sulfonic acids grafted to the polymer backbone. Polymer backbones include those based on a polyester, a poly(meth)acrylate, a polystyrene, a poly(styrene-(meth)acrylate), a polycarbonate, a polyamide, a polyimide, a polyurethane, a polyvinyl alcohol, or a copolymer comprising at least one of these polymeric backbones. Additionally, the surfactant can be anionic, cationic, zwitterionic, or non-ionic.

Exemplary cationic surfactants include but are not limited to alkyl primary, secondary, and tertiary amines, alkanolamides, quaternary ammonium salts, alkylated imidazolium, and pyridinium salts. Additional examples of the cationic surfactant include primary to tertiary alkylamine salts such as, for example, monostearylammonium chloride, distearylammonium chloride, tristearylammonium chloride; quaternary alkylammonium salts such as, for example, monostearyltrimethylammonium chloride, distearyldimethylammonium chloride, stearyldimethylbenzylammonium chloride, monostearyl-bis(polyethoxy)methylammonium chloride; alkylpyridinium salts such as, for example, N-cetylpyridinium chloride, N-stearylpyridinium chloride; N,N-dialkylmorpholinium salts; fatty acid amide salts such as, for example, polyethylene polyamine; and the like.

Exemplary anionic surfactants include alkyl sulfates, alkyl sulfonates, fatty acids, sulfosuccinates, and phosphates. Examples of an anionic surfactant include anionic surfactants having a carboxyl group such as sodium salt of alkylcarboxylic acid, potassium salt of alkylcarboxylic acid, ammonium salt of alkylcarboxylic acid, sodium salt of alkylbenzenecarboxylic acid, potassium salt of alkylbenzenecarboxylic acid, ammonium salt of alkylbenzenecarboxylic acid, sodium salt of polyoxyalkylene alkyl ether carboxylic acid, potassium salt of polyoxyalkylene alkyl ether carboxylic acid, ammonium salt of polyoxyalkylene alkyl ether carboxylic acid, sodium salt of N-acylsarcosine acid, potassium salt of N-acylsarcosine acid, ammonium salt of N-acylsarcosine acid, sodium salt of N-acylglutamic acid, potassium salt of N-acylglutamic acid, ammonium salt of N-acylglutamic acid; anionic surfactants having a sulfonic acid group; anionic surfactants having a phosphonic acid; and the like.

The nonionic surfactant can be, e.g., ethoxylated fatty alcohols, alkyl phenol polyethoxylates, fatty acid esters, glycerol esters, glycol esters, polyethers, alkyl polyglycosides, amineoxides, or a combination thereof. Exemplary nonionic surfactants include fatty alcohols (e.g., cetyl alcohol, stearyl alcohol, cetostearyl alcohol, oleyl alcohol, and the like); polyoxyethylene glycol alkyl ethers (e.g., octaethylene glycol monododecyl ether, pentaethylene glycol monododecyl ether, and the like); polyoxypropylene glycol alkyl ethers (e.g., butapropylene glycol mononyl ether); glucoside alkyl ethers (e.g., decyl glucoside, lauryl glucoside, octyl glucoside); polyoxyethylene glycol octylphenol ethers (e.g., Triton X-100 (octyl phenol ethoxylate)); polyoxyethylene glycol alkylphenol ethers (e.g., nonoxynol-9); glycerol alkyl esters (e.g., glyceryl laurate); polyoxyethylene glycol sorbitan alkyl esters (e.g., polysorbates such as sorbitan monolaurate, sorbitan monopalmitate, sorbitan monostearate, sorbitan tristearate, sorbitan monooleate, and the like); sorbitan alkyl esters (e.g., polyoxyethylene sorbitan monolaurate, polyoxyethylene sorbitan monopalmitate, polyoxyethylene sorbitan monostearate, polyoxyethylene sorbitan monooleate, and the like); cocamide ethanolamines (e.g., cocamide monoethanolamine, cocamide diethanolamine, and the like); amine oxides (e.g., dodecyldimethylamine oxide, tetradecyldimethylamine oxide, hexadecyl dimethylamine oxide, octadecylamine oxide, and the like); block copolymers of polyethylene glycol and polypropylene glycol (e.g., poloxamers available under the trade name Pluronics, available from BASF); polyethoxylated amines (e.g., polyethoxylated tallow amine); polyoxyethylene alkyl ethers such as polyoxyethylene stearyl ether; polyoxyethylene alkylene ethers such as polyoxyethylene oleyl ether; polyoxyalkylene alkylphenyl ethers such as polyoxyethylene nonylphenyl ether; polyoxyalkylene glycols such as polyoxypropylene polyoxyethylene glycol; polyoxyethylene monoalkylates such as polyoxyethylene monostearate; bispolyoxyethylene alkylamines such as bispolyoxyethylene stearylamine; bispolyoxyethylene alkylamides such as bispolyoxyethylene stearylamide; alkylamine oxides such as N,N-dimethylalkylamine oxide; and the like Zwitterionic surfactants (which include a cationic and anionic functional group on the same molecule) include, for example, betaines, such as alkyl ammonium carboxylates (e.g., $[(CH_3)_3N^+—CH(R)COO^-]$ or sulfonates (sulfo-betaines) such as $[RN^+(CH_3)_2(CH_2)_3SO_3^-]$, where R is an alkyl group). Examples include n-dodecyl-N-benzyl-N-methylglycine $[C_{12}H_{25}N^+(CH_2C_6H_5)(CH_3)CH_2COO^-]$, N-allyl N-benzyl N-methyltaurines $[C_nH_{2n+1}N^+(CH_2C_6H_5)(CH_3)CH_2CH_2SO_3^-]$.

The solvent is an aqueous solvent or an organic solvent. The aqueous solvent is, e.g., water. The organic solvent includes an alcohol (e.g., methanol, ethanol, isopropanol, and the like), dimethylsulfone, acetone, an acetate, dimethsulfoxide, dimethylformamide, γ-butyrolactone, tetrahydrofuran, propylene carbonate, ethylene glycol, an ether, an aromatic solvent (e.g., benzene, toluene, p-xylene, ethylbenzene, and the like), or a combination comprising at least one of the foregoing. The solvent is selected based on the constituents of composition 76. In some embodiments, the solvent is water, an alcohol (monohydric such a C1-C4 alcohol or polyhydric such as glycols), a carboxylic acid (e.g., formic acid, acetic acid, and the like), and the like, or a combination thereof.

Membrane 4 can be various thicknesses or widths. A thickness of the membrane 4 is from 10 nanometers (nm) to 1 millimeters (mm), specifically 10 nm to 10 micrometers (μm), and more specifically 10 nm to 100 nm. The width of membrane 4 can be from 10 nm to 10 μm. It is contemplated that the substrate can be planar or have other shapes such as a curved shape, circular, toroidal, convex, concave, and the like shapes. Without being limited thereto, dimensions of components of single molecule electrograph, single molecule filter, or single molecule detector include from length 0.1 nm to 10 μm μm, outer diameter 10 nm to 1 μm, inner diameter 1 nm to 10 nm, wall thickness 1 nm to 100 nm, width 1 nm to 10 μm, thickness 1 nm to 10 μm of substrate first layer, 1 nm to 10 um of membrane first layer, 1 nm to 10 μm of interfacial layer, gate electrode width 1 nm to 100 μm, and the like.

In an embodiment, the semiconductor of Si, GaN, InGaN, InAs, GaAs independently includes a dopant, e.g., a p-dopant, an n-dopant, an electron acceptor—(such as Boron), or an electron donor (such as phosphorous). An amount of the dopant is from $10^{12}$ dopant atoms $cm^{-3}$ to $10^{18}$ dopant atoms $cm^{-3}$, more specifically from $10^{14}$ dopant atoms $cm^{-3}$ to $10^{17}$ dopant atoms $cm^{-3}$.

Additives such as the buffer, surfactant, and the like are present in composition 76 in an amount from 0 weight percent (wt %) to 20 wt %, specifically 0 wt % to 10 wt %, and more specifically 0 wt % to 5 wt %, based on a weight of composition 76.

Single molecule 78 can be present in composition 76 in a concentration from 1 picomolar to 1 molar, specifically from 1 nanomolar to 1 micromolar, and more specifically less than 1 micromolar. It will be appreciated that these are bulk concentration in composition 76 disposed in first compartment 88, and the concentration as disposed in tubular aperture 18 will be greater than these quantities in some embodiments.

In an embodiment, with reference to FIG. 15, FIG. 16, FIG. 17, FIG. 18, FIG. 19, and FIG. 20, a process for making single molecule filter includes: providing substrate 100 including first layer 22 comprising first surface 6 and second layer 26 disposed on first layer 22 and including second surface 8; removing a portion of second layer 26 to form membrane aperture 10 bounded by membrane wall 32; disposing catalyst 102 on first surface 6 of first layer 22; contacting catalyst 102 with a precursor; forming nanocolumn 110 interposed between catalyst 102 and first layer 22, nanocolumn 110 including a reaction product of the precursor; oxidizing a portion of first layer 22 at first surface 6 to form interfacial layer 20, interfacial layer 20 including a semiconductor oxide; oxidizing a portion of nanocolumn 110 to form nanotube 12 disposed on interfacial layer 20, nanotube 12 including: the semiconductor oxide, first end 14 disposed on first surface 6 of substrate 100; and second end 16 disposed distal to first surface 6; removing nanocolumn 110 to form tubular aperture 18 extending along nanotube 12 from first end 14 to second end 16, tubular aperture 18 provided to communicate single molecule 78 from second end 16 of nanotube 12 to membrane aperture 10; extending membrane wall 32 through first layer 22 by removing a portion of first layer 22 so that membrane aperture 10 and tubular aperture 18 provide communication of single molecule 76 from second end 16 of nanotube 12 to second surface 8 of membrane 4 through tubular aperture 18 and membrane aperture 10 to make single molecule filter 2.

The precursor is provided to form nanocolumn 110 disposed on substrate 100 in a presence of catalyst 102. Exemplary precursors include silane ($SIH_4$), $SiCl_4$, and the like.

According to an embodiment, a silicon on insulator (SOI) wafer having different crystallographic silicon handle and device layers is used as the substrate 100.

A silicon etchant is used to etch the handle layer to form a membrane consisting of the silicon device and the buried oxide layers. Exemplary silicon etchants include sodium hydroxide (KOH) and the like.

Nanoparticles of a catalytic metal 102 are dispersed on substrate 100 to serve as catalytic regions for the growth of semiconductor nanocolumns 110. Exemplary catalytic metals include gold and the like.

Nanocolumn 110 is grown to a length from 10 nm to 100 μm. A chemical process is used to grow or deposit a dielectric on the surface of nanocolumn 110. High-k dielectric material such as, e.g., silicon dioxide, hafnium dioxide, aluminum oxide, and the like can be used. Subsequent dielectric etch and re-oxidation can be used to form inner diameter ID1 of the nanotube 12 with a selected size.

A vapor phase silicon etchant such as $XeF_2$ can be used to remove the nanocolumn 110 and semiconductor material below nanocolumn 110 in first layer. As a result, nanotube 12 includes tubular aperture 18 having a continuous opening from second end to first end and in fluid communication with membrane aperture.

In an embodiment, with reference to FIG. 21, FIG. 22, FIG. 23, FIG. 24, FIG. 25, and FIG. 26, a process for making single molecule electrograph 50 includes providing substrate 100 including first layer 22 comprising first surface 6 and second layer 26 disposed on first layer 22 and including second surface 8; removing a portion of second layer 26 to form membrane aperture 10 bounded by membrane wall 32; disposing catalyst 102 on first surface 6 of first layer 22; contacting catalyst 102 with a precursor; forming nanocolumn 110 interposed between catalyst 102 and first layer 22, nanocolumn 110 including a reaction product of the precursor; oxidizing a portion of first layer 22 at first surface 6 to form interfacial layer 20, interfacial layer 20 including a semiconductor oxide; oxidizing a portion of nanocolumn 110 to form nanotube 12 disposed on interfacial layer 20, nanotube 12 including: the semiconductor oxide, first end 14 disposed on first surface 6 of substrate 100; and second end 16 disposed distal to first surface 6; removing nanocolumn 110 to form tubular aperture 18 extending along nanotube 12 from first end 14 to second end 16, tubular aperture 18 provided to communicate single molecule 78 from second end 16 of nanotube 12 to membrane aperture 10; disposing active element 52 (e.g., MoS2, GaN, doped Si, and the like) by a growth process (e.g., depositing by disposing exfoliated material, vapor phase growth (e.g. vapor deposition), epitaxial growth, and the like); subjecting active element 52 to an electron beam to size active element such that nanotube 12 occupies, e.g., 90% of a width of active element 52; disposing (e.g., by metal deposition and performing photolithography (e.g., electron beam lithography) source electrode 54 and drain electrode 58; disposing gate dielectric 64 (e.g., a conformal high-k dielectric such as $Al_2O_3$) to overlap with source electrode 54 and drain electrode 58; disposing gate electrode 62 on gate dielectric by gas phase deposition; subjecting gate electrode 62 to photolithography to provide a selected shape to gate electrode 62; subjecting first layer 22 to an etchant (e.g., $XeF_2$) to form membrane 4 and to remove nanocolumn 110 such that the process includes extending membrane wall 32 through first layer 22 by removing a portion of first layer 22 so that membrane aperture 10 and tubular aperture 18 provide communication of single molecule 76 from second end 16 of nanotube 12 to second surface 8 of membrane 4 through tubular aperture 18 and membrane aperture 10 to make single molecule electrograph 50.

It is contemplated that conventional semi-conductor processing methodologies can be used to make single molecule electrograph 50 and single molecule filter 2.

The process also can include connecting a power supply to source electrode 54, drain electrode 58, gate electrode 62, primary electrode 80, secondary electrode 82, and the like. Moreover, in an embodiment, a power supply can be electrically connected to an array that includes a plurality of single molecule electrographs 50, single molecule filter 2, or a combination thereof, that can be disposed on a substrate. It is contemplated that in the array individual single molecule electrographs 50 or single molecule filters 2 are independently addressable or aggregately addressable, e.g., to deliver composition 76, to control a voltage to an electrode, to detect ion current therefrom, to detect drain current changes therefrom, and the like.

In an embodiment, single molecule electrograph 50 can be disposed in packaging that includes electrical connections to an external power supply or electrometer such that wire bonds can be attached to source electrode 54, drain electrode 58, and gate electrode 62 to provide continuity to electrical wires or traces on a printed circuit board.

A plurality of electrographs can be disposed on a single substrate and connected to a plurality of power sources by interconnect metal layers or wire bonds bridging a plurality of source electrode 54, drain electrode 58, and gate electrode 62. A plurality of single molecule electrographs 50 can be disposed in multiple packages that are disposed on a printed circuit board such that external power sources and electrometers can be connected to wires, e.g., soldered to metal traces on the board. Connections to the board provide supply power and provide for measurement of drain current and for acquisition of drain current for further processing by a controller or computer processor.

In an embodiment, a process for making single molecule detector 70 includes disposing single molecule electrographs 50 or single molecule filters 2 in container 72, and providing electrodes therein.

In an embodiment, a process for detecting single molecule 78 includes: providing single molecule detector 2 disposing composition 76 including single molecule 78 in first compartment 88; and communicating single molecule 78 from first compartment 88 to second compartment 90 through tubular aperture 18 and membrane aperture 10 to detect single molecule 78. Composition 76 further can include the fluid in which single molecule 78 is disposed, the solvent, and the plurality of charged species including the ionic liquid, the plurality of ions, or a combination thereof. The process can include communicating the charged particles through tubular aperture 18 to second compartment 90; contacting secondary electrode 82 with the charged particles in second compartment 90; and producing a first ion current at secondary electrode 82 in response to contact with the charged particles. The process also can further include communicating single molecule 78 through tubular aperture 18 to second compartment 90; and decreasing the first ion current to a second ion current in response to a presence of single molecule 78 in tubular aperture 18. In some embodiments, the process includes determining whether single molecule 78 was communicated from first compartment 88 to second compartment 90 based on a difference between the first ion current and the second ion current; and optionally producing a chromatogram based on the difference between the first ion current and the second ion current as a function of time.

According to some embodiments, the process further includes subjecting single molecule 78 to a stimulus prior to communicating single molecule 78 through tubular aperture 18, wherein the stimulus includes an electric field, hydrostatic pressure, electroosmotic pressure, a concentration gradient, or a combination thereof. Producing the electric field can be accomplished by applying a potential difference across primary electrode 80 and secondary electrode 82. Producing the hydrostatic pressure can be accomplished by pressurizing the first compartment at a pressure greater than the second compartment. In some embodiments, the electric field and hydrostatic pressure are applied in combination. In certain embodiments, the stimulus is pulsed so that the stimulus is sometimes applied at a first amplitude and applied at a subsequent time at a second amplitude. A period of the first amplitude or second amplitude can be selected to obtain a selected value for communicating single molecule 78 through tubular aperture 18 of nanotube 12 of single molecule filter 2 single molecule electrograph 50.

Figure 27:
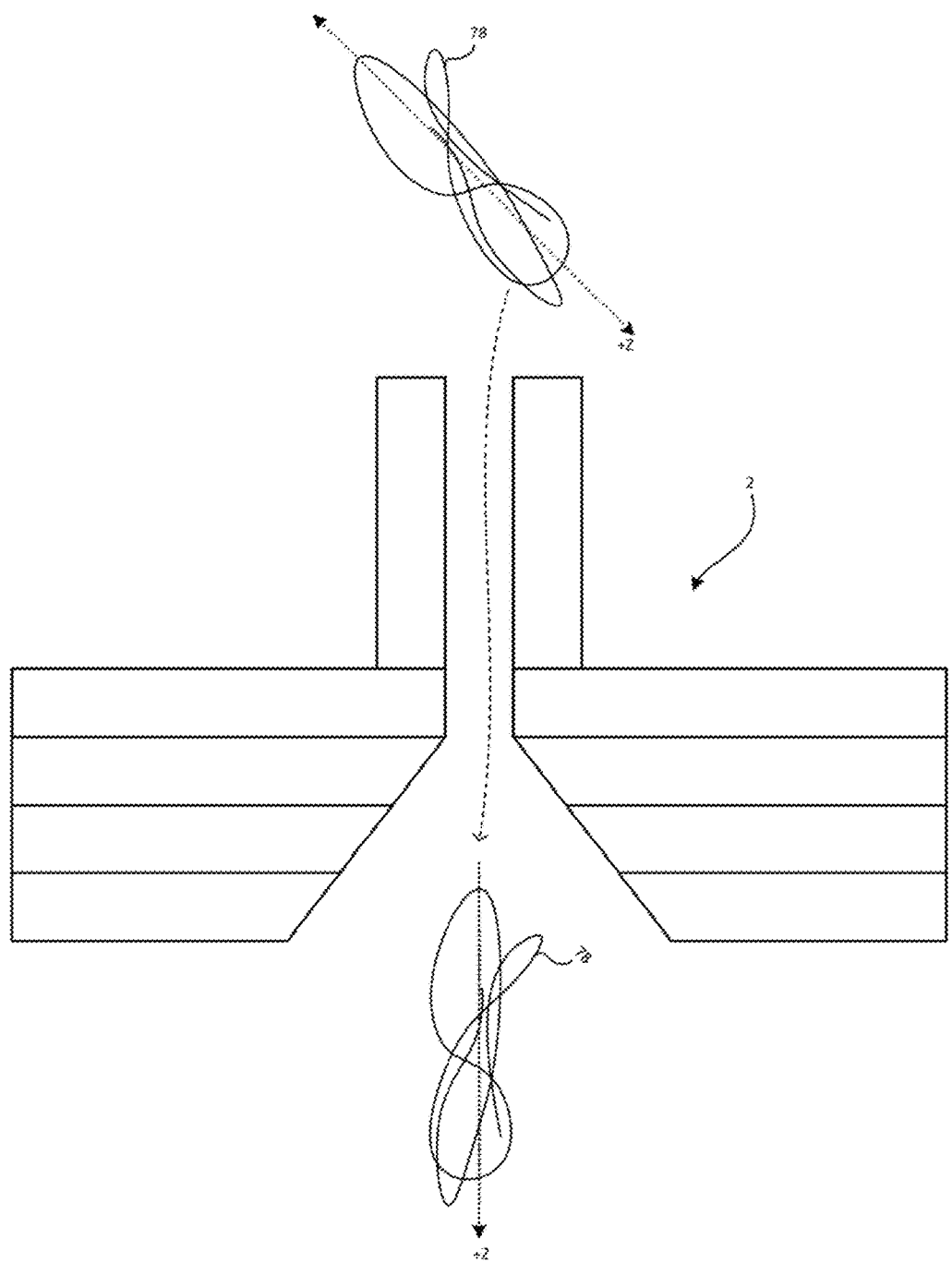
FIG. 27 shows communication of a single molecule through a single molecule filter.

As shown in FIG. 27, single molecule 78, e.g., a protein, having a three-dimensional conformation that includes a long molecular axis Z and short molecular axis Y is communicated through tubular aperture 18 of nanotube 12 from first position 120 in first compartment 88 to second position 122 in second compartment 90 of container 72. Without wishing to be bound by theory, it is believed that inner diameter ID1 of nanotube 12 can be selected to selectively communicate a certain orientation of single molecule 78 through tubular aperture 18 and membrane aperture 10. According to an embodiment, single molecule 78 is communicated through tubular aperture 18 when long molecular axis Z is substantially aligned with inner wall 34 of nanotube 12, and single molecule 78 is not communicated through tubular aperture 18 when long molecular axis Y is substantially aligned with inner wall 34 of nanotube 12. Here, selection of an orientation of single molecule 78 is due to size exclusion of single molecule 78 by a size of inner diameter ID1 of nanotube 12. In some embodiments, single molecule 78 is selectively communicated through tubular aperture 18 and membrane aperture 10 based on a polarity, hydrophilicity, or molecular charge of single molecule 78 relative to that of inner wall 34 of nanotube 12. In a particular embodiment, single molecule 78 is selectively communicated through tubular aperture 18 and membrane aperture 10 based on the hydrophilicity, wherein will, relative to a particular amino acids such as lysine) and is communicated through tubular aperture 18 that also is hydrophilic but would not be communicated through nanotube 12 if tubular aperture 18 was hydrophobic. According to an embodiment, communication of single molecule 78 through tubular aperture 18 is selected by size of single molecule 78, hydrophilicity of single molecule 78, or combination thereof in view of a size exclusion of tubular aperture 18, hydrophilicity of inner wall 34 of tubular aperture 18, or combination thereof.

Figure 28:
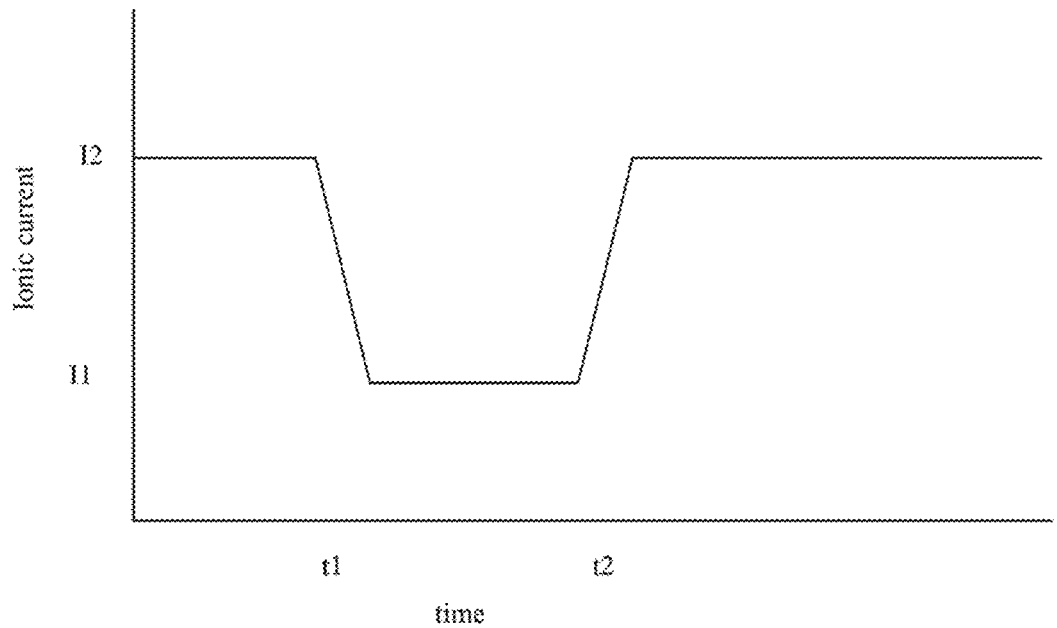
FIG. 28 shows a graph of ion current versus time.

As shown in FIG. 28 (a graph of ion current versus time), communication of single molecule 78 through tubular aperture 18 of single molecule filter 2 is determined from a change in ion current produced at secondary electrode 82. Here, tubular aperture 18 communicates charged particles in composition 76 from first compartment 88 to in second compartment 90 and produce ion current I2 at secondary electrode 82. At time t1, single molecule 78 is present in tubular aperture 18 and decreases a flux of charged particles communicated through tubular aperture 18 to decrease the ion current at secondary electrode 82 from ion current I2 to ion current I1. From time t1 to time t2, single molecule 78 is present in tubular aperture 18 such that the ion current at secondary electrode 82 is maintained less than ion current I2. At time t2, single molecule 78 is absent in tubular aperture 18 having been fully communicated into second compartment 90 such that the ion current at secondary electrode 82 attains ion current I2 due to an increase in flux of charged particles through tubular aperture 18 in an absence of single molecule 78 therein.

Figure 29:
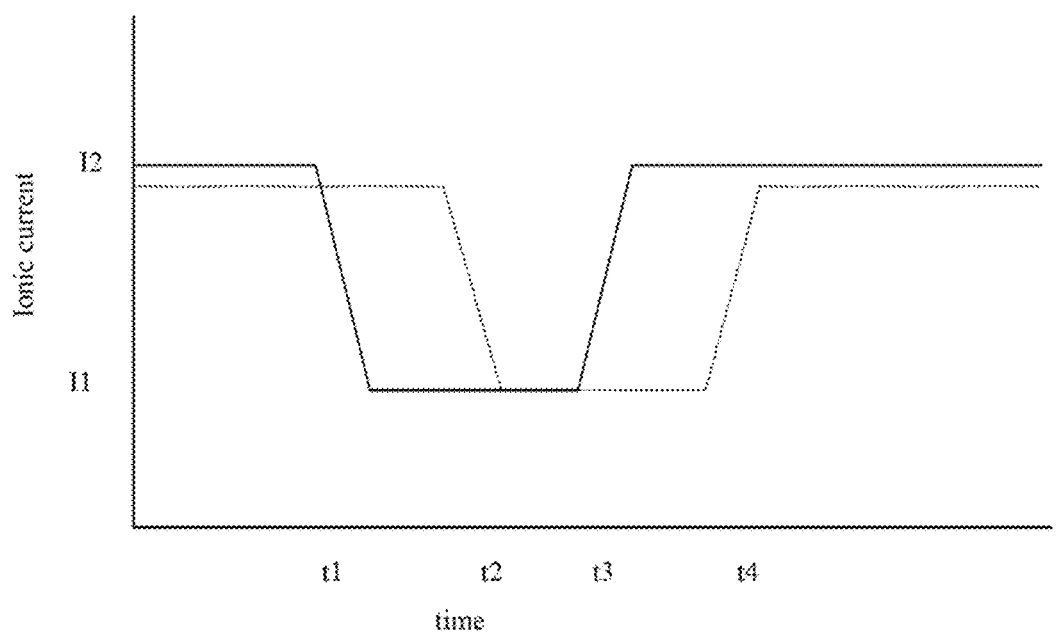
FIG. 29 shows a graph of ion current versus time.

In an embodiment, with reference to FIG. 29 (a graph of ion current versus time), composition 76 includes first single molecule 76 and second single molecule 76, wherein first single molecule 76 has a first size that is less than a second size of second single molecule 76. Here, due to the size difference in first single molecule 76 and second single molecule 76, first single molecule 76 is communicated through tubular aperture 18 from time t1 to time t3, and second single molecule 76 is communicated through tubular aperture 18 from time t2 to time t4. It will be appreciated that at time t3, first single molecule 76 is fully communicated to second compartment 90, and second single molecule 76 is present in tubular aperture 18 such that from time t3 to time t4 first single molecule 76 is isolated and separated from second single molecule 76 in second compartment 90. Accordingly, from time t3 to time t4, first single molecule 76 can be removed from second compartment 90 before arrival at time t4 of second single molecule 76 to produce two pure samples that respectively include first single molecule 76 and second single molecule 76. As a result, single molecule filter 2 can be used to select or separate single molecules in a plurality of single molecules based on size.

Figure 30:
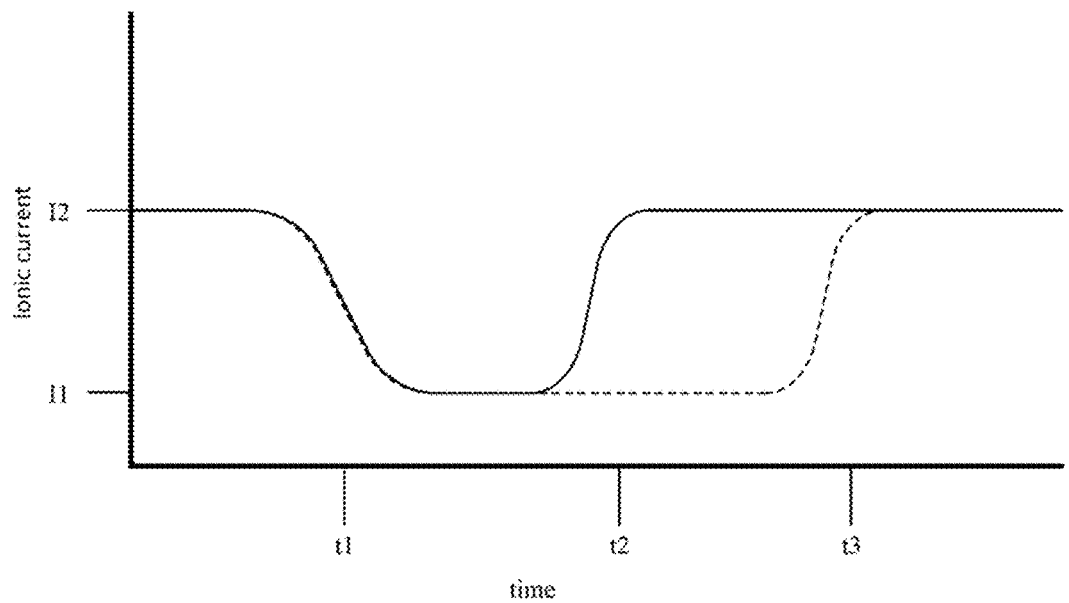
FIG. 30 shows a graph of ion current versus time.

In an embodiment, with reference to FIG. 30 (a graph of ion current versus time), composition 76 includes first single molecule 76 and second single molecule 76, wherein first single molecule 76 has a first hydrophilicity that is different than a second hydrophilicity of second single molecule 76. Here, due to a difference in hydrophilicity of first single molecule 76 and second single molecule 76, first single molecule 76 is communicated through tubular aperture 18 from time t1 to time t3, and second single molecule 76 is communicated through tubular aperture 18 from time t1 to time t3. It will be appreciated that at time t2 to time t3, first single molecule 76 is fully communicated to second compartment 90, and second single molecule 76 is present in tubular aperture 18 such that from time t2 to time t3 first single molecule 76 is isolated and separated from second single molecule 76 in second compartment 90. Accordingly, from time t2 to time t3, first single molecule 76 can be removed from second compartment 90 before arrival at time t3 of second single molecule 76 to produce two pure samples that respectively include first single molecule 76 and second single molecule 76. As a result, single molecule filter 2 can be used to select or separate single molecules in a plurality of single molecules based on hydrophilicity that can produce a difference of retention time in tubular aperture 18.

As shown in FIG. 28, FIG. 29, and FIG. 30, single molecule filter 2 selectively communicates one single molecule 78 through tubular aperture 18 at a time. It is contemplated that a configuration or, e.g., surface properties of inner wall 34 of nanotube 12 can be selected to provide communication of a plurality of single molecules 78 through tubular aperture 18 with selectivity toward a property of such single molecule 78 such as size, hydrophilicity, charge, and the like.

Figure 31:
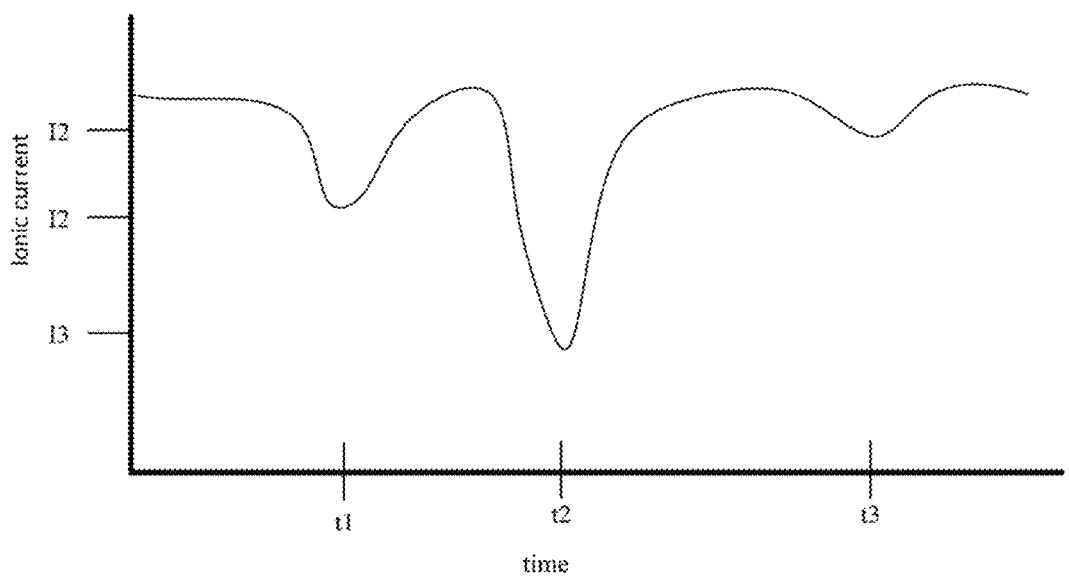
FIG. 31 shows a graph of ion current versus time.

With reference to FIG. 31 (a graph of ion current versus time), composition 76 that includes a plurality of single molecule 76 can be disposed in first compartment 88 of container 72 such that different single molecules 76 or communicated through tubular aperture 18 of nanotube 12, e.g., at time t1, time t2, time t3, and the like. Here, ion current peaks at time t1, time t2, and time t3 are fully resolved and do not overlap such that temporal separation of different single molecules 76 in composition 76 is provided by single molecule filter 2.

Figure 33:
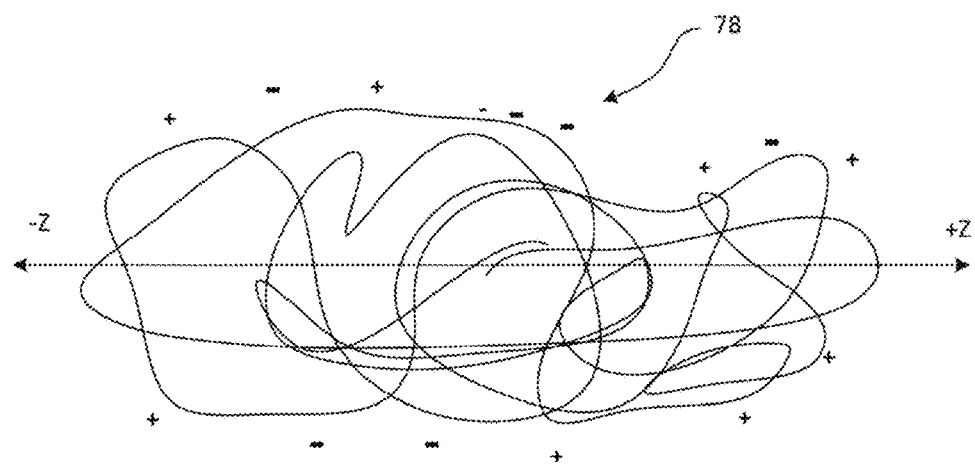
FIG. 33 shows a single molecule and surface charge distribution of the single molecule.
Figure 32:
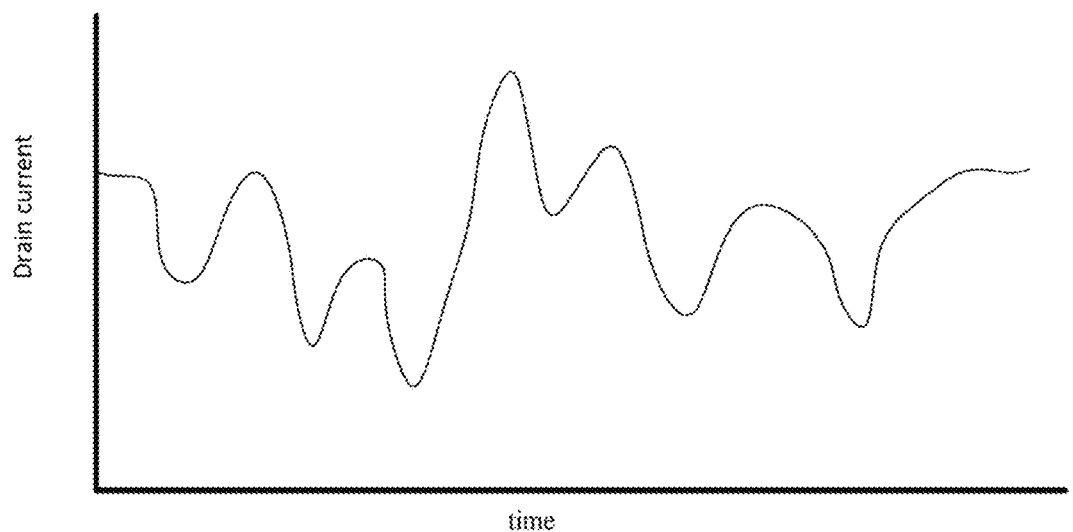
FIG. 32 shows a graph of drain current versus time.

In an embodiment, as shown in FIG. 32 (a graph of drain current versus time), communication of single molecules 78 in composition 76 through tubular aperture 18 of single molecule electrograph 50 is determined from a change in drain current produced at drain electrode 58. Here, tubular aperture 18 communicates single molecule 78 from first compartment 88 to second compartment 90. In single molecule 78 (e.g., a protein) can have a conformation, charge distribution, and long axis (indicated by labels +Z and −Z) shown in FIG. 33. Accordingly, the drain current from single molecule electrograph 50 is initially I0 at time t0. As single molecule 78 is communicated through tubular aperture 18 from +Z to −Z, the drain current decreases or increases due to a polarity of single molecule 78 as a function of length along the long axis of single molecule 78. In this manner, data shown in FIG. 32 can be analyzed to determine a charge distribution of single molecule 78, a composition or sequence of amino acids in a protein or monomers in a polymer in single molecule 78, and the like.

In an embodiment, as shown in FIG. 32, the drain current can span greater than 7 orders of magnitude, more specifically the drain current can be from 1 femtoampere (fA) to 1 milliampere (mA). A response time of single molecule electrograph 50 can be from less than 1 nanosecond (ns) to 1 millisecond (ms).

The articles and processes herein are illustrated further by the following Examples, which are non-limiting.

EXAMPLES

Example 1. Transport of Charged Particles Across a Nanotube

Figure 34:
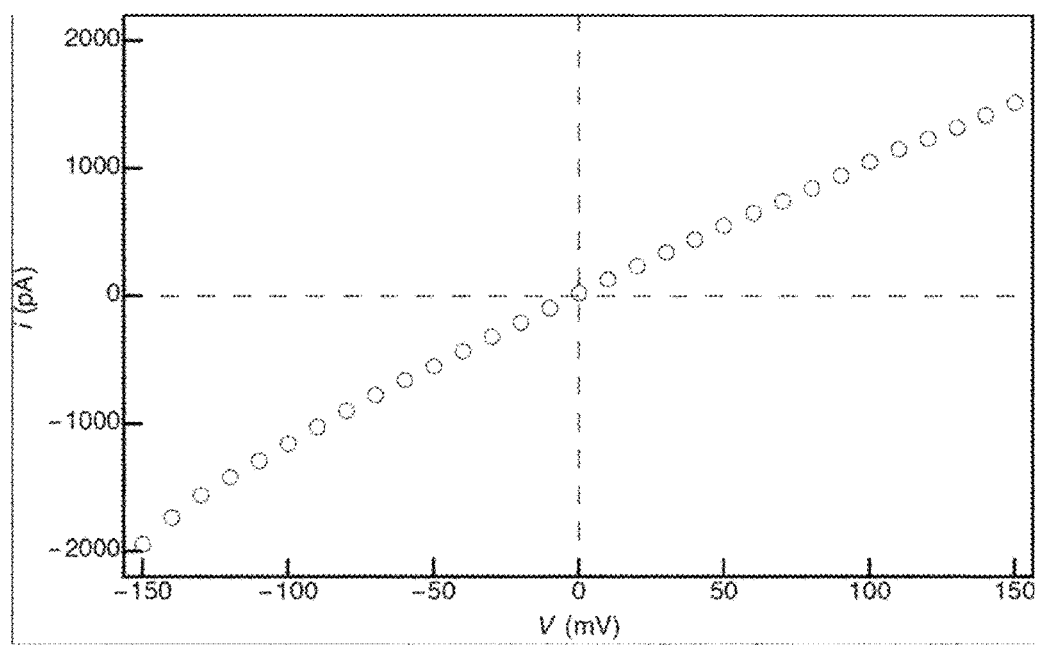
FIG. 34 shows a graph of ion current versus voltage according to Example 1.

A single nanotube was placed in a container such that the tube was the only pathway for transport of charged particles. The container included two compartments; each including an electrode placed on opposing open ends of the nanotube and also included a 100 mM NaCl fluid. Communication of charged particles through the nanotube occurred in response to an electric field subjected to the nanotube by application of an electric potential to the electrodes. Communication of the charged particles produced an ionic current that was measured. As the relative voltage on the electrodes was changed from −150 mV to +150 mV, the ionic current increased as shown in FIG. 34, which is a graph of ion current versus voltage. A polarity of the ionic current changed at 0 V, and the capacitance of the nanotube caused rectification at negative voltages.

Example 2. Calculation of Electrostatic Profile of Biomolecules Passing Through a Nanotube Poisson-Boltzmann calculations are used to estimate a surface charge on two protein biomarkers (a first protein biomarker 200 (shown in FIG. 35) that is indicative of an ischemic stroke and a second protein biomarker 202 (shown in FIG. 35) that is indicative of hemorrhagic strokes) disposed in 150 mM NaCl and subjected to communication through a 6-nm inner diameter nanotube of a single molecule filter. Hydrophilic residues on the surface of the protein biomarkers (200, 202) include amino acid side chains that are charged or neutral. In some cases, the charge on protein biomarkers (200, 202) may be influenced by a local environment such as a concentration of protein biomarkers (200, 202) in the fluid. Furthermore, the surface charge may be influenced by confinement, e.g., from passing protein biomarkers (200, 202) through the nanotube that has a certain dimension or size. The calculations yield the surface charge on protein biomarkers (200, 202) as protein biomarkers (200, 202) is communicated through the 6-nm inner diameter nanotube. Magnitudes or profiles of surface charge along a long axis of protein biomarkers (200, 202) are substantially different such that protein biomarkers (200, 202) can be unique identified or characterized.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A single molecule filter comprising:
    a membrane comprising:
        a first surface;
        a second surface; and
        a membrane aperture disposed in the membrane and traversing the membrane from the first surface to the second surface, the membrane aperture provided to communicate a single molecule across the membrane; and
    a nanotube disposed on the membrane and comprising:
        a first end disposed on the first surface of the membrane;
        a second end disposed distal to the first surface; and
        a tubular aperture extending along the nanotube from the first end to the second end, the tubular aperture provided to communicate the single molecule from the second end of the nanotube to the membrane aperture.

2. The single molecule filter of claim 1, further comprising an interfacial layer disposed on the first surface and interposed between the first end of the nanotube and the first surface of the membrane.

3. The single molecule filter of claim 1, wherein the membrane comprises a plurality of layers.

4. The single molecule filter of claim 3, wherein the plurality of layers comprises:
    a first layer comprising:
        a first semiconductor; and
        the first surface; and
    a second layer opposing the first layer and comprising:
        a second semiconductor; and
        the second surface.

5. The single molecule filter of claim 4, wherein the plurality of layers further comprises an intermediate layer interposed between the first layer and the second layer.

6. The single molecule filter of claim 4, wherein the membrane further comprises a membrane wall that bounds the membrane aperture.

7. The single molecule filter of claim 5, wherein the intermediate layer comprises an oxide of the first semiconductor.

8. The single molecule filter of claim 1, wherein the nanotube comprises an inner wall that bounds the tubular aperture.

9. The single molecule filter of claim 8, wherein the nanotube further comprises a length, an outer diameter, an inner diameter, and an aspect ratio that is a ratio of the length to the inner diameter,
    wherein the aspect ratio is greater than 200.

10. The single molecule filter of claim 8, wherein the nanotube further comprises a semiconductor.

11. The single molecule filter of claim 10, wherein the semiconductor comprises an oxide.

12. The single molecule filter of claim 10, wherein the inner wall of the nanotube comprises a functional group attached to the semiconductor.

13. The single molecule filter of claim 1, wherein the nanotube is vertically aligned to the first surface.

14. A single molecule detector comprising:
a single molecule filter comprising:
a membrane comprising:
a first surface;
a second surface; and
a membrane aperture disposed in the membrane and traversing the membrane from the first surface to the second surface, the membrane aperture provided to communicate a single molecule across the membrane;
a nanotube disposed on the membrane and comprising:
a first end disposed on the first surface of the membrane;
a second end disposed distal to the first surface; and
a tubular aperture extending along the nanotube from the first end to the second end, the tubular aperture provided to communicate the single molecule from the second end of the nanotube to the membrane aperture;
a primary electrode disposed:
proximate to and opposing the second end of the nanotube, and distal to the second surface; and
a secondary electrode disposed:
proximate to and opposing the second surface,
distal to the nanotube, and
opposing the primary electrode.

15. The single molecule detector of claim 14, further comprising a container in which the single molecule filter, the primary electrode, and the secondary electrode are disposed.

16. The single molecule detector of claim 15, further comprising:
a first compartment; and
a second compartment,
wherein the single molecule filter partitions the container and separates the first compartment from the second compartment such that the tubular aperture and the membrane aperture solely communicate the single molecule between the first compartment and the second compartment.

17. A process for detecting a single molecule, the process comprising:
providing a single molecule detector that comprises:
a single molecule filter comprising:
a membrane comprising:
a first surface;
a second surface; and
a membrane aperture disposed in the membrane and traversing the membrane from the first surface to the second surface, the membrane aperture provided to communicate a single molecule across the membrane;
a nanotube disposed on the membrane and comprising:
a first end disposed on the first surface of the membrane;
a second end disposed distal to the first surface; and
a tubular aperture extending along the nanotube from the first end to the second end, the tubular aperture provided, to communicate the single molecule from the second end of the nanotube to the membrane aperture;
a primary electrode disposed:
proximate to and opposing the second end of the nanotube, and
distal to the second surface;
a secondary electrode disposed;
proximate to and opposing the second surface,
distal to the nanotube, and
opposing the primary electrode; and
a container in which the single molecule filter, the primary electrode, and the secondary electrode are disposed, the single molecule filter partitioning the container into a first compartment and a second compartment with the single molecule filter separating the first compartment from the second compartment such that the tubular aperture and the membrane aperture solely communicate the single molecule between the first compartment and the second compartment;
disposing a composition comprising the single molecule in the first compartment; and
communicating the single molecule from the first compartment to the second compartment through the tubular aperture and the membrane aperture to detect the single molecule.

18. The process of claim 17, wherein the composition further comprises a fluid in the which the single molecule is disposed.

19. The process of claim 18, wherein the fluid comprises:
a solvent;
a plurality of charged species comprising an ionic liquid, a plurality of ions, or a combination comprising at least one of the foregoing; or
a combination comprising at least one of the foregoing.

20. The process of claim 19, wherein the fluid includes the charged particles, and the process further comprises:
communicating the charged particles through the tubular aperture to the second compartment;
contacting the second electrode with the charged particles in the second compartment; and
producing a first ion current at the second electrode in response to contact with the charged particles.

21. The process of claim 20, further comprising:
communicating the single molecule through the tubular aperture to the second compartment; and
decreasing the first ion current to a second ion current in response to a presence of the single molecule in the tubular aperture.

22. The process of claim 21, further comprising determining whether the single molecule was communicated from the first compartment to the second compartment based on a difference between the first ion current and the second ion current.

23. The process of claim 22, further comprising producing a chromatogram based on the difference between the first ion current and the second ion current as a function of time.

24. The process of claim 21, further comprising subjecting the single molecule to a stimulus prior to communicating the single molecule through the tubular aperture.

25. The process of claim 24, wherein the stimulus comprises, an electric field, hydrostatic pressure, electroosmotic pressure, a concentration gradient, a thermal gradient or a combination comprising at least one of the foregoing.

26. The process of claim 25, further comprising producing the electric field by applying a potential difference across the first electrode and the second electrode.

27. The process of claim 25, further comprising producing the hydrostatic pressure by pressurizing the first compartment at a pressure greater than the second compartment.

28. A process for making a single molecule filter, the process comprising:
   providing a substrate comprising:
      a first layer comprising a first surface; and
      a second layer disposed on the first layer and comprising a second surface;
   removing a portion of the second layer to form a membrane aperture bounded by a membrane wall;
   disposing a catalyst on the first surface of the first layer;
   contacting the catalyst with a precursor;
   forming a nanocolumn interposed between the catalyst and the first layer, the nanocolumn comprising a reaction product of the precursor;
   oxidizing a portion of the first layer at the first surface to form an interfacial layer, the interfacial layer comprising a semiconductor oxide;
   oxidizing a portion of the nanocolumn to form a nanotube disposed on the interfacial layer, the nanotube comprising:
      the semiconductor oxide;
      a first end disposed on the first surface of the membrane; and
      a second end disposed distal to the first surface;
   removing the nanocolumn to form a tubular aperture extending along the nanotube from the first end to the second end, the tubular aperture provided to communicate a single molecule, from the second end of, the nanotube to the membrane aperture; and
   extending the membrane wall through the first layer by removing a portion of the first layer so that the membrane aperture and the tubular aperture provide communication of the single molecule from the second end of the nanotube to the second surface of the across the membrane through the tubular aperture and the membrane aperture to make the single molecule filter.

\* \* \* \* \*